(12) United States Patent
Kasahara

(10) Patent No.: US 9,323,036 B2
(45) Date of Patent: Apr. 26, 2016

(54) IMMERSION MICROSCOPE OBJECTIVE AND MICROSCOPE USING THE SAME

(71) Applicant: OLYMPUS CORPORATION, Tokyo (JP)

(72) Inventor: Takashi Kasahara, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 480 days.

(21) Appl. No.: 13/845,041

(22) Filed: Mar. 17, 2013

(65) Prior Publication Data

US 2013/0271829 A1 Oct. 17, 2013

(30) Foreign Application Priority Data

Apr. 12, 2012 (JP) ................................. 2012-091378
Mar. 15, 2013 (JP) ................................. 2013-053106

(51) Int. Cl.
*G02B 21/02* (2006.01)
*G02B 21/06* (2006.01)
*G02B 21/33* (2006.01)
*G02B 27/00* (2006.01)
*G01N 21/64* (2006.01)

(52) U.S. Cl.
CPC ............... *G02B 21/02* (2013.01); *G02B 21/06* (2013.01); *G02B 21/33* (2013.01); *G02B 27/0068* (2013.01); *G01N 21/648* (2013.01); *G01N 21/6458* (2013.01)

(58) Field of Classification Search
CPC .. G02B 21/02; G02B 21/025; G02B 21/0076; G02B 21/16; G02B 21/33; G02B 27/0068; G01N 21/6458; G01N 21/648; G01N 21/6428; G01N 21/6447
See application file for complete search history.

(56) References Cited

U.S. PATENT DOCUMENTS

| 4,232,941 A * | 11/1980 | Tojo ............................... 359/658 |
| 2003/0076600 A1* | 4/2003 | Watanabe ....................... 359/656 |
| 2006/0082896 A1* | 4/2006 | Mandai et al. ................. 359/661 |
| 2012/0113524 A1* | 5/2012 | Kasahara et al. ............. 359/656 |

FOREIGN PATENT DOCUMENTS

| JP | 2002-098903 A | 4/2002 |
| JP | 2002-148519 A | 5/2002 |
| JP | 2006-113486 A | 4/2006 |

* cited by examiner

*Primary Examiner* — Stephone B Allen
*Assistant Examiner* — Adam W Booher
(74) *Attorney, Agent, or Firm* — Holtz, Holtz & Volek PC

(57) ABSTRACT

A microscope objective comprises in order from an object side, a first lens group, a second lens group, and a third lens group. The first lens group includes a first cemented lens, and at least one positive single lens, the second lens group includes a second cemented lens, and the third lens group includes a first lens component and a second lens component. A positive lens and a meniscus lens are cemented in the first cemented lens. A surface nearest to an image side of the first lens component is a concave surface, and a surface nearest to the object side of the second lens component is a concave surface. The first lens component and the second lens component are disposed such that the both concave surfaces are face-to-face, and the following conditional expression (1) is satisfied.

$$0.5 < (n_0/n_{1o})/NA_{ob} < 0.65 \qquad (1)$$

9 Claims, 15 Drawing Sheets

IMMERSION MICROSCOPE OBJECTIVE AND MICROSCOPE USING THE SAME

CROSS-REFERENCE TO RELATED APPLICATION

The present application is based upon and claims the benefit of priority from the prior Japanese Patent Application Nos. 2012-091378 filed on Apr. 12, 2012 and 2013-053106 filed on Mar. 15, 2013; the entire contents of which are incorporated herein by reference.

BACKGROUND OF THE INVENTION

1. Field of the Invention

The present invention relates to an immersion microscope objective, and a microscope using the same.

2. Description of the Related Art

In the field of research of biology, suppressing invasive potential toward living cells to be as low as possible, and being capable to observe an extremely minute structure (hereinafter, 'microscopic structure') of a specimen, have always been sought. In recent years, for observing the microscopic structure of a specimen, there have been an increasing number of applications for observing a specimen by using a weak light. Light diffracted from the microscopic structure is a light having a large angle of diffraction. When an image is formed by using diffracted light having a large angle of diffraction, it is possible to observe the microscopic structure.

One of the applications for observing a specimen by using weak light is a total internal reflection fluorescence observation. In the total internal reflection fluorescence observation, evanescent light is used. Evanescent light is generated by making incident illumination light on a boundary surface having different refractive index, at an angle of incidence not smaller than certain degrees, and by making the illumination light undergo total internal reflection. The evanescent light has a peculiarity of being localized in an area smaller than a wavelength on an opposite side of the illumination light with respect to the boundary surface, and not propagating in a free space.

In the total internal reflection fluorescence observation, light is made to be incident on a cover glass such that the total internal reflection occurs at a boundary surface of the cover glass and a specimen. As the light is incident on the cover glass and undergoes total internal reflection, evanescent light is permeated from the boundary surface toward the specimen. An area through which the evanescent light is permeated is an area of about a wavelength of light. In such manner, an area illuminated by excitation light is restricted to the area through which the evanescent light is permeated, or the area of about the wavelength of light. In the total internal reflection fluorescence observation, fluorescence is not generated in an area except the limited illuminated area. Therefore, in the total internal reflection fluorescence observation, fluorescence observation with less background noise is possible.

Furthermore, the evanescent light has a peculiarity that a depth of an area through which the evanescent light is permeated changes according to an angle (an angle of incidence) of light which is incident on the boundary surface. Larger the angle of incidence of light, narrower is the area through which the evanescent light is permeated. When the angle of incidence of light is made large, since it is possible to reduce the background noise, even brighter observation with a high resolution is possible. The total internal reflection fluorescence observation having such characteristics has been used for observing a movement and an activity of various substances in a biological cell.

In the total internal reflection fluorescence observation, a microscope objective with a large numerical aperture is used. For instance, when the specimen is a cell, a refractive index of a cell is in a range of 1.33 to 1.4. Therefore, for letting the total internal reflection occur at the boundary surface of the cover glass and the specimen, the numerical aperture of the microscope objective is required to be at least 1.4 or larger than 1.4. Moreover, for narrowing the area through which the evanescent light is permeated, it is necessary to make large the angle of incidence of light which is incident on the boundary surface. For fulfilling the abovementioned requirements, it is desirable that the numerical aperture of the microscope objective is large.

Moreover, even in an observation other than the total internal reflection fluorescence observation, when it is possible to take in diffracted light with a large angle of diffraction, it is possible to observe the microscopic structure. Therefore, it is desirable that the numerical aperture of the microscope objective is large.

As a microscope objective with a large numerical aperture, immersion microscope objectives disclosed in Japanese Patent Application Laid-open Publication Nos. 2002-098903, 2002-148519, and 2006-113486 are available.

SUMMARY OF THE INVENTION

To solve the abovementioned issues, and to achieve the object, an immersion microscope objective according to the present invention comprises in order from an object side a first lens group, a second lens group, and a third lens group, wherein the first lens group includes a first cemented lens, and at least one positive single lens, and the second lens group includes a second cemented lens, and changes a divergent bundle of rays to a convergent bundle of rays, and the third lens group includes in order from the object side, a first lens component and a second lens component, and a positive lens and a meniscus lens are cemented in the first cemented lens, and a surface nearest to an image side of the first lens component is a concave surface directed toward the image side, and a surface nearest to the object side of the second lens component is a concave surface directed toward the object side, and the first lens component and the second lens component are disposed such that the concave surface of the first lens component and the concave surface of the second lens component are face-to-face, and the following conditional expression (1) is satisfied.

$$0.5 < (n_0/n_{1o})/NA_{ob} < 0.65 \tag{1}$$

where, $NA_{ob}$ denotes an object-side numerical aperture of the microscope objective, $n_0$ denotes a refractive index for a d-line of a medium on the object side of the positive lens, and $n_{1o}$ denotes a refractive index for a d-line of the positive lens.

Moreover, a microscope according to the present invention comprises a light source, an illumination optical system, a main-body section, an observation optical system, and
a microscope objective, wherein
the immersion microscope objective described above is used for the microscope objective.

According to the present invention, it is possible to provide an immersion microscope objective having a large numerical aperture, and in which, a spherical aberration and a chromatic aberration, are corrected sufficiently, and a microscope in which such immersion microscope objective has been used.

DETAILED DESCRIPTION OF THE INVENTION

Figure 1:
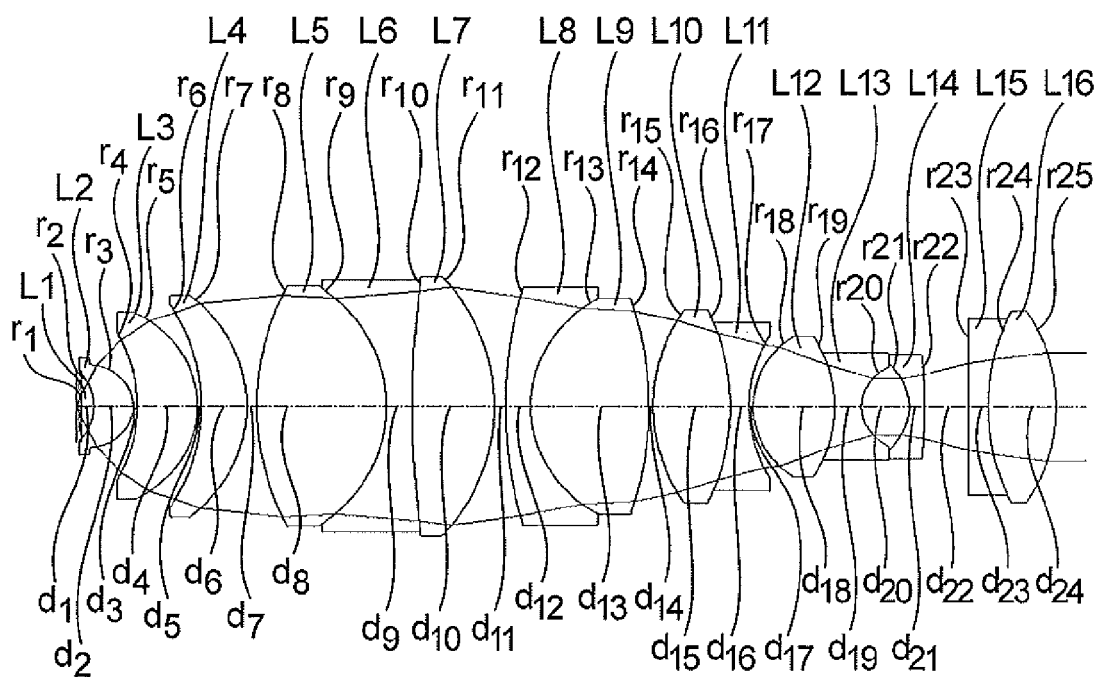
FIG. 1 is a cross-sectional view along an optical axis showing an optical arrangement of an immersion microscope objective according to a first example of the present invention.

An immersion microscope objective according to a first aspect of the present invention comprises in order from an object side, a first lens group, a second lens group, and a third lens group, and the first lens group includes a first cemented lens, and at least one positive single lens, and the second lens group includes a second cemented lens, and changes a divergent bundle of rays to a convergent bundle of rays, and the third lens group includes in order from the object side, a first lens component and a second lens component, and a positive lens and a meniscus lens are cemented in the first cemented lens, and a surface nearest to an image side of the first lens component is a concave surface directed toward the image side, and a surface nearest to the object side of the second lens component is a concave surface directed toward the object side, and the first lens component and the second lens component are disposed such that the concave surface of the first lens component and the concave surface of the second lens component are face-to-face, and the following conditional expression (1) is satisfied.

$$0.5 < (n_0/n_{1o})/NA_{ob} < 0.65 \quad (1)$$

where, $NA_{oo}$ denotes an object-side numerical aperture of the microscope objective, $n_0$ denotes a refractive index for a d-line of a medium on the object side of the positive lens, and $n_{1o}$ denotes a refractive index for a d-line of the positive lens.

The immersion microscope objective (hereinafter, called appropriately as 'objective') according to the first aspect includes in order from the object side, the first lens group, the second lens group, and the third lens group. Moreover, the first lens group includes the first cemented lens and at least one positive single lens. Moreover, the positive lens and the meniscus lens are cemented in the first cemented lens. The object side means a specimen side.

When an object-side numerical aperture (hereinafter, called simply as 'numerical aperture') of the objective is made large, it is possible to make incident light of even larger angle of divergence (angle of diffraction) from a specimen to the objective. As a result, it is possible to observe a microscopic structure even more minutely. Moreover, in a total internal reflection fluorescence observation, a fluorescence observation with less background noise is possible. However, a height of a light ray with a large angle of divergence is high the first lens group. When such light ray is bent sharply in the first lens group, an aberration of high order is susceptible to occur in the first lens group.

Therefore, in the objective according to the present embodiment, by forming the first lens group with the first cemented lens and at least one positive single lens, the light ray having a large angle of divergence is bent gradually by the first cemented lens and the positive single lens. By making such arrangement, it is possible to suppress the aberration of high order from occurring substantially.

Moreover, the second lens group is let to include the second cemented lens. As it has been described above, an arrangement is made such that in the first lens group, the light ray with a large angle of divergence is bent gradually. Therefore, bundle of rays which emerges from the first lens group is not a convergent bundle of rays. So, in the second lens group, the divergent bundle of rays is changed to the convergent bundle of rays. Here, since the second lens group includes the second cemented lens, it is possible to change the divergent bundle of rays to the convergent bundle of rays, and to carry out correction of a chromatic aberration by the second cemented lens. One of the actions of the second lens group is to change the divergent bundle of rays to the convergent bundle of rays. Therefore, in a case in which, another lens which generates such action is there other than in the second cemented lens, such lens is also included in the second lens group.

Moreover, the third lens group includes in order from the object side, the first lens component and the second lens component, and the surface nearest to the image side of the first lens component is a concave surface directed toward the image side, and the surface nearest to the object side of the second lens component is a concave surface directed toward the object side, and the first lens component and the second lens component are disposed such that the concave surface of the first lens component and the concave surface of the second lens component are face-to-face.

By disposing the first lens component and the second lens component such that the concave surface of the first lens component and the concave surface of the second lens component are face-to-face, it is possible to bring a lens arrangement of the third lens group close to a lens arrangement of Gauss type. Here, since the divergent bundle of rays is changed to the convergent bundle of rays in the second lens group, the height of the light ray is low at a position of the first lens component and at a position of the second lens component. Therefore, by the concave surface of the first lens component and the concave surface of the second lens component, it is possible to make Petzval's sum small.

Moreover, in the objective according to the present embodiment, the following conditional expression (1) is satisfied.

$$0.5<(n_0/n_{1o})/NA_{ob}<0.65 \quad (1)$$

where, $NA_{ob}$ denotes an object-side numerical aperture of the microscope objective, $n_0$ denotes a refractive index for a d-line of a medium on the object side of the positive lens, and $n_{1o}$ denotes refractive index for a d-line of the positive lens.

By satisfying conditional expression (1), it is possible to make the refractive index of the positive lens sufficiently high. Here, the positive lens is positioned nearest to the object side. For instance, when the object side of the positive lens is filled with an immersion liquid, a refractive index of a medium on the object side of the positive lens is a refractive index of the immersion liquid. In this case, when the refractive index of the positive lens is kept to be sufficiently high, it is possible to make an arrangement such that a difference in the refractive index of the immersion liquid and the refractive index of the positive lens does not become large. As a result, even in a case in which, the numerical aperture has been made large; it is possible to suppress an aberration which occurs at a boundary surface of the positive lens and the medium (immersion liquid) to be small.

When an upper limit value of conditional expression (1) is surpassed, since the difference between the refractive index of the positive lens and the refractive index of the medium (immersion liquid) becomes excessively large, it is not possible to suppress the aberration which occurs at the boundary surface to be small. Therefore, it is not possible to make the numerical aperture large.

When a lower limit value of conditional expression (1) is not reached, it is not possible to make the numerical aperture sufficiently large. Therefore, it is difficult to achieve high resolution. Moreover, in the total internal reflection fluorescence observation, it is not possible to narrow an area through which the evanescent light is permeated. As a result, it is difficult to carry out observation with less background noise.

It is preferable that the following conditional expression (1') is satisfied instead of conditional expression (1).

$$0.5<(n_0/n_{1o})/NA_{ob}<0.595 \quad (1')$$

In this manner, in the objective according to the present embodiment, it is possible to make the numerical aperture large while maintaining a favorable image forming performance. Therefore, it is possible to observe the microscopic structure of a specimen. Moreover, in the total internal reflection fluorescence observation, since it is possible to narrow the area through which the evanescent light is permeated, it is possible to carry out observation with less background noise.

Moreover, in the objective according to the present embodiment, it is preferable that the first lens group includes the plurality of positive single lenses, and the following conditional expression (2) is satisfied.

$$1<r_{1c}/r_{1i}<2 \quad (2)$$

where, $r_{1c}$ denotes a radius of curvature of a cemented surface of the first cemented lens, and $r_{1i}$ denotes a radius of curvature of an image-side surface of the first cemented lens.

Conditional expression (2) is a conditional expression for securing an appropriate refractive power for the first cemented lens, while suppressing an occurrence of Petzval's sum. The cemented surface of the first cemented lens has a negative refractive power. It is preferable to make small Petzval's sum in the first cemented lens by the negative refractive power. However, in a case in which, the numerical aperture is large, when the negative refractive power is made excessively large; a height of a light ray becomes high. Therefore, a large positive refractive power becomes necessary in lenses, which positioned on the image side of the cemented lens, in the first lens group, and occurrence of the aberration of high order cannot be suppressed. Moreover, in the lens group which positioned on the image side of the first lens group, the occurrence of the spherical aberration and the chromatic aberration cannot be suppressed.

Therefore, by satisfying conditional expression (2), it is possible to prevent the negative refractive power at the cemented surface from becoming excessively large. As a result, it is possible to lower down the height of the light ray to a height where the occurrence of the aberration of high order in the lenses, which positioned on the image side of the first cemented lens, in the first lens group, and the occurrence of the spherical aberration and the chromatic aberration in the lens group which positioned on the image side of the first lens group.

When an upper limit value of conditional expression (2) is surpassed, the radius of curvature of the cemented surface becomes excessively large (the negative refractive power becomes excessively small). Therefore, it is not possible to make Petzval's sum small. As a result, it becomes difficult to carry out correction of Petzval's sum (to make Petzval's sum small) in the lenses, which positioned on the image side of the first cemented lens, in the first lens group, or in the lens group which positioned on the image side of the second lens group.

When a lower limit value of conditional expression (2) is not reached, the radius of curvature of the cemented surface becomes excessively small (negative refractive power becomes excessively large). Therefore, it is not possible to lower down the height of the light ray to a height where the occurrence of the aberration of high order in the lenses, which positioned on the image side of the first cemented lens, in the first lens group, and the occurrence of the spherical aberration and the chromatic aberration in the lens group which positioned on the image side of the first lens group, are suppressed.

In the objective according to the present embodiment, the Petzval's sum is made smaller by the first lens group and the third lens group. Therefore, in the first lens group, insufficiency of correction of Petzval's sum is permissible in the first lens group.

Moreover, it is preferable that the following conditional expression (2') is satisfied instead of conditional expression (2).

$$1.25 < r_{1c}/r_{1i} < 1.5 \quad (2')$$

Moreover, in the objective according to the present embodiment, it is preferable that the following conditional expression (3) is satisfied.

$$0.2 < (d_{1o} \times n_{1o})/(d_{1i} \times n_{1i}) < 1 \quad (3)$$

where, $d_{1o}$ denotes an optical axial thickness of the positive lens, $n_{1o}$ denotes the refractive index for a d-line of the positive lens, $d_{1i}$ denotes an optical axial thickness of the meniscus lens, and $n_{1i}$ denotes a refractive power for a d-line of the meniscus lens.

Conditional expression (3) is a conditional expression for achieving an appropriate height of a light ray even in a case in which, the numerical aperture is made large. By imparting an appropriate thickness to the positive lens, it is possible to make a light ray with a large angle of divergence incident on the objective. On the other hand, by suppressing appropriately the thickness of the meniscus lens, it is possible to bend a light ray where the height of the light ray does not become high. Therefore, it is possible to lower the height of the light ray without bending the light ray sharply, in an optical system on the image side of the first cemented lens. As a result, the occurrence of the spherical aberration and the chromatic aberration is suppressed.

When an upper limit value of conditional expression (3) is surpassed, the thickness of the meniscus lens becomes excessively thin. In this case, it is necessary to bend sharply a light ray having a large angle of divergence, and to lower the height of the light ray, at an image-side lens surface of the meniscus lens. Therefore, the occurrence of the aberration of high order cannot be suppressed in the first cemented lens.

When a lower limit value of conditional expression (3) is not reached, the thickness of the positive lens becomes excessively thin. Therefore, it is not possible to make a light ray having a large angle of divergence incident on the positive lens. Or, the thickness of the meniscus lens becomes excessively large. In this case, it is not possible to lower a height of a light ray emerging from the meniscus lens. As a result, it becomes difficult to suppress the occurrence of the spherical aberration and the chromatic aberration in an optical system on the image side of the first cemented lens.

Moreover, it is more preferable that the following conditional expression (3') is satisfied instead of conditional expression (3).

$$0.25 < (d_{1o} \times n_{1o})/(d_{1i} \times n_{1i}) < 0.4 \quad (3')$$

Moreover, in the objective according to the present embodiment, it is preferable that the following conditional expression (4) is satisfied.

$$0.2 < f_1/d_1 < 0.45 \quad (4)$$

where, $f_1$ denotes a focal length of the first lens group, and $d_1$ denotes an overall length of the first lens group.

Conditional expression (4) is a conditional expression for achieving an appropriate height of a light ray even in a case in which, the numerical aperture is made large. In the objective with a large numerical aperture, the height of a light ray which passes through the first lens group or the second lens group becomes extremely high. Therefore, suppressing the occurrence of the spherical aberration and the chromatic aberration is susceptible to become difficult. Moreover, when the light ray is bent sharply to lower the height of the light ray, the aberration of high order occurs in the first lens group. By satisfying conditional expression (4), it is possible to impart an appropriate focal length and an appropriate overall length to the first lens group. As a result, it is possible to lower down the height of a light ray to a height where the occurrence of the spherical aberration and the chromatic aberration is suppressed, without bending the light ray sharply.

When an upper limit value of conditional expression (4) is surpassed, the focal length of the first lens group becomes excessively large. In this case, bending the light ray gently and lowering the height of a light ray are incompatible. Therefore, it becomes difficult to suppress simultaneously the occurrence of the spherical aberration and the chromatic aberration.

When a lower limit value of conditional expression (4) is not reached, the overall length of the first lens group becomes excessively long. Therefore, it becomes difficult to correct the chromatic aberration and an aberration of curvature in an optical system which positioned on the image side of the first lens group.

Moreover, it is more preferable that the following conditional expression (4') is satisfied instead of conditional expression (4).

$$0.33 < f_1/d_1 < 0.4 \quad (4')$$

Moreover, in the objective according to the present embodiment, it is preferable that the following conditional expression (5) is satisfied.

$$0.2 < n_{1H} - n_{1L} < 0.6 \quad (5)$$

where, $n_{1H}$ denotes the highest refractive index for a d-line of the positive single lens, and $n_{1L}$ denotes the lowest refractive index for a d-line of the positive single lens.

Conditional expression (5) is a conditional expression which is preferable for suppressing the occurrence of the aberration of high order and the chromatic aberration simultaneously. Higher the refractive index of an optical material of the positive single lens used in the first lens group, easier it is to suppress the occurrence of the aberration of high order. However, since few optical materials with high refractive index have a large Abbe's number, it is difficult to suppress the occurrence of the chromatic aberration by only an optical material having a high refractive index. Therefore, by disposing the plurality of single lenses, and combining an optical material having a high refractive index and an optical material having a lower refractive index, it is possible to suppress simultaneously the occurrence of the aberration of high order and the chromatic aberration.

When an upper limit value of conditional expression (5) is surpassed, many optical materials used in the first lens group become optical materials having a high refractive index. In this case, since the optical materials used in the first lens group is only an optical material for which Abbe's number is extremely small, it becomes difficult to suppress the occurrence of the chromatic aberration.

When a lower limit value of conditional expression (5) is not reached, many optical materials used in the first lens group are optical materials having a low refractive index. In this case, since the radius of curvature of the lens in the first lens group has to be made small, it becomes difficult to suppress simultaneously the occurrence of the aberration of high order and the chromatic aberration.

Moreover, in the objective according to the present embodiment, it is preferable that the second lens component includes an object-side lens and a third cemented lens, and a height of an axial marginal ray is the maximum at the third cemented lens of the second lens component, and is the minimum at a surface nearest to the object side of the second lens component, and the following conditional expression (6) is satisfied.

$$0 < f_{32o}/f_{32} < 0.45 \quad (6)$$

where, $f_{32o}$ denotes a focal length of the object-side lens, and $f_{32}$ denotes a focal length of the second lens component.

In the objective according to the present embodiment, the third lens group includes the first lens component and the second lens component, and the first lens component and the second lens component are disposed such that the concave surface of the first lens component and the concave surface of the second lens component are face-to-face. Moreover, the second lens component includes the object-side lens and the third cemented lens.

As mentioned heretofore, the cemented surface of the cemented lens of the first lens group has a negative refractive power. It is preferable to correct Petzval's sum (to make Petzval's sum small) by the negative refractive power. However, in the objective according to the present embodiment, since the numerical aperture of the lens is large, it is difficult to correct Petzval's sum by the first lens group only.

Therefore, it is necessary to correct Petzval's sum by the third lens group. For correcting the Petzval's sum, the height of a light ray in the second lens group is kept to be high, and the height of a light ray in the third lens group is kept to be low. Moreover, concave surfaces which are face-to-face are provided in the third lens group. It is preferable to correct Petzval's sum by making such an arrangement.

Here, as an optical system in which, the convex surfaces are arranged face-to-face; an optical system of Gauss type is available. In the optical system of Gauss type, two cemented lenses having a meniscus shape are disposed such that concave surfaces of the two cemented lenses are face-to-face. By making such an arrangement, it is possible to correct favorably the spherical aberration and a curvature of field. Moreover, correction of Petzval's sum is carried out by using a fact that the height of a light ray at a concave surface is low. However, in the optical system of Gauss type, since a refractive power of the concave surface becomes large, the aberration of high order is susceptible to occur.

Therefore, in the objective according to the present embodiment, an arrangement is made such that the lens component having the concave surface directed toward the object side, or in other words, the second lens component, includes the object-side lens and the third cemented lens. Here, the object-side lens is disposed at a position facing the first lens component, and an object-side surface thereof is directed toward the concave surface on the object side.

In such manner, by the second lens component including the third cemented lens, it is possible to bring a lens arrangement of the third lens group further closer to Gauss type. In addition, items possible to suppress appropriately a refractive power of the concave surface of the object-side lens.

Moreover, in the objective according to the present embodiment, the conditional expression (6) is satisfied.

Conditional expression (6) is a conditional expression for suppressing Petzval's sum to be small. By suppressing appropriately the focal length of the object-side lens, it is possible to correct Petzval's sum while suppressing the occurrence of the aberration of high order.

When an upper limit value of conditional expression (6) is surpassed, the focal length of the object-side lens group becomes excessively large. In this case, it is not possible to lower the height of a light ray at the third lens group sufficiently. Therefore, correction of Petzval's sum and correction of the aberration of curvature become difficult.

When a lower limit value of conditional expression (6) is not reached, the focal length of the object-side lens becomes excessively small. In this case, since the refractive power at the concave surface of the object-side lens becomes excessively large, suppressing the occurrence of the aberration of high order becomes difficult.

Moreover, in the objective according to the present embodiment, it is preferable that one of the first lens group, the second lens group, and the third lens group moves along an optical axis.

A refractive index of a cover glass and a refractive index of an immersion liquid are not exactly the same. Therefore, when there is a variation in a thickness of the cover glass or when there is a change in temperature of an environment in which the microscope objective is used, there is a fluctuation in aberration due to a change in a refractive index of the immersion liquid or a refractive index of an optical material which used for the lens.

Therefore, by moving one of the first lens group, the second lens group, and the third lens group along the optical axis, it is possible to provide an immersion microscope objective having a large numerical aperture which is capable of maintaining favorable image forming performance even when there is a variation in the thickness of the cover glass or when there is a change in temperature of the environment in which the immersion microscope objective is used, and a microscope using the immersion microscope objective.

A microscope according to the present embodiment is a microscope which includes a light source, an illumination optical system, a main-body section, an observation optical system, and a microscope objective, and any of the immersion microscope objectives described above is used in the microscope objective.

Examples of the immersion microscope objective according to the present invention will be described below in detail by referring to the accompanying diagrams. However, the present invention is not restricted to the examples described below.

Figure 14:
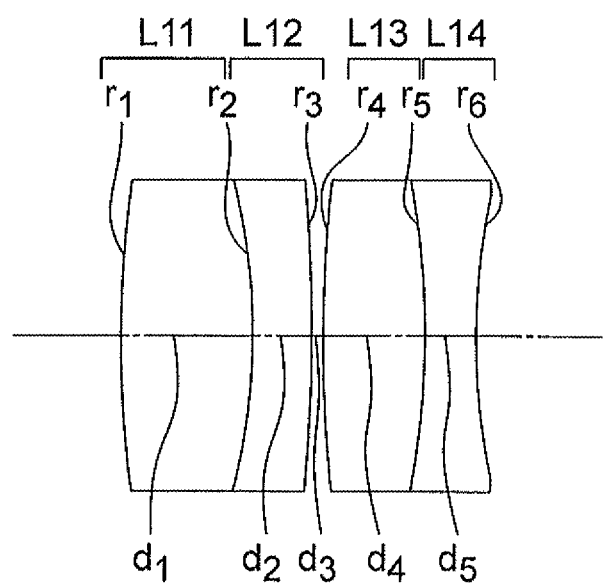
FIG. 14 is a cross-sectional view of a tube lens.

A first example, a second example, a third example, and a fourth example (hereinafter, 'embodiments from the first embodiment to the fourth embodiment') of the immersion microscope objective according to the present invention will be described below. Cross sections along an optical axis showing an optical arrangement of the immersion microscope objectives according to the examples from the first example to the fourth example are shown in FIG. 1, FIG. 2, FIG. 3, and FIG. 4 (hereinafter, 'FIG. 1 to FIG. 4'). In the cross-sectional views, reference numerals L1, L2, L3, ..., L16 denote lenses. Moreover, FIG. 14 is a cross-sectional view of a tube lens.

The immersion microscope objectives of the examples from the first example to the fourth example are infinity-corrected microscope objectives. In an infinity-corrected microscope objective, since a bundle of rays which is emerged from the microscope objective becomes parallel, image is not formed in itself. Therefore, the parallel bundle of rays is converged by a tube lens as shown in FIG. 14. Moreover, an image of a sample surface is formed at a position at which the parallel bundle of rays is converged.

Next, an objective according to the first example will be described below. The objective according to the first example, as shown in FIG. 1, includes in order from an object side, a first lens group, and an image-side lens group which is positioned on an image side of the first lens group.

The first lens group includes in order from the object side, a planoconvex positive lens L1, a positive meniscus lens L2 having a convex surface directed toward the image side, a positive meniscus lens L3 having a convex surface directed toward the image side, and a positive meniscus lens L4 having a convex surface directed toward the image side. Here, the planoconvex positive lens L1 and the positive meniscus lens L2 are cemented. This cemented lens is the first cemented lens.

The image-side lens group includes in order from the object side, a biconvex positive lens L5, a biconcave negative lens L6, a biconvex positive lens L7, a negative meniscus lens L8 having a convex surface directed toward the object side, a biconvex positive lens L9, a biconvex positive lens L10, a biconcave negative lens L11, a biconvex positive lens L12, a biconcave negative lens L13, a negative meniscus lens L14 having a convex surface directed toward the image side, a planoconcave negative lens L15, and a biconvex positive lens L16.

Here, the biconvex positive lens L5, the biconcave negative lens L6, and the biconvex positive lens L7 are cemented. Moreover, the negative meniscus lens L8 and the biconvex positive lens L9 are cemented. Moreover, the biconvex positive lens L10 and the biconcave negative lens L11 are cemented. Moreover, the biconvex positive lens L12 and the biconcave negative lens L13 are cemented. Moreover, the planoconcave negative lens L15 and the biconvex positive lens L16 are cemented.

Moreover, the image-side lens group includes a second lens group and a third lens group. Here, the second lens group includes a second cemented lens, and has an action of changing a divergent bundle of rays to a convergent bundle of rays. In the objective according to the first example, by a cemented lens of lenses from the biconvex positive lens L5 up to the biconvex positive lens L7, the divergent bundle of rays is changed to the convergent bundle of rays. Accordingly, this cemented lens can be regarded as the second lens group. Also, this cemented lens is the second cemented lens.

Changing of a divergent bundle of rays to a convergent bundle of rays is carried out by two cemented lenses which include lenses from the biconvex positive lens L5 up to the biconvex positive lens L9. Accordingly, the two cemented lenses can be regarded as the second lens group. Furthermore, changing of a divergent bundle of rays to a convergent bundle of rays is carried out by three cemented lenses which include lenses from the biconvex positive lens L5 up to the biconvex positive lens L11. Therefore, the three cemented lenses can be regarded as the second lens group.

On the other hand, the third lens group includes a first lens component and a second lens component. Moreover, a surface nearest to the image side of the first lens component is a concave surface directed toward the image side, and a surface nearest to the object side of the second lens component is a concave surface directed toward the object side, and the first lens component and the second lens component are disposed such that the concave surface of the first lens component and the concave surface of the second lens component are face-to-face.

Accordingly, in a cemented lens of the biconvex positive lens L12 and the biconcave negative lens L13, a surface on the image side of the biconcave negative lens L13 being a concave surface directed toward the image side, this cemented lens can be regarded as the first lens component. Moreover, in the negative meniscus lens L14, a surface on the object side being a concave surface directed toward the object side, the negative meniscus lens L14 can be regarded as the second lens component.

While it is connected to an arrangement of the second lens group as well, the first lens component can be regarded to further include at least one of a cemented lens of the negative meniscus lens L8 and the biconvex positive lens L9, and a cemented lens of the biconvex positive lens L10 and the biconcave negative lens L11.

Moreover, the second lens component further includes a cemented lens of the planoconcave negative lens L15 and the biconvex positive lens L16 as the third cemented lens. In this case, since the negative meniscus lens L14 is positioned on the object side of the third cemented lens, the negative meniscus lens L14 becomes the object-side lens.

A position of each of the first lens group G1, the second lens group G2, and the third lens group G3 is fixed.

Figure 2:
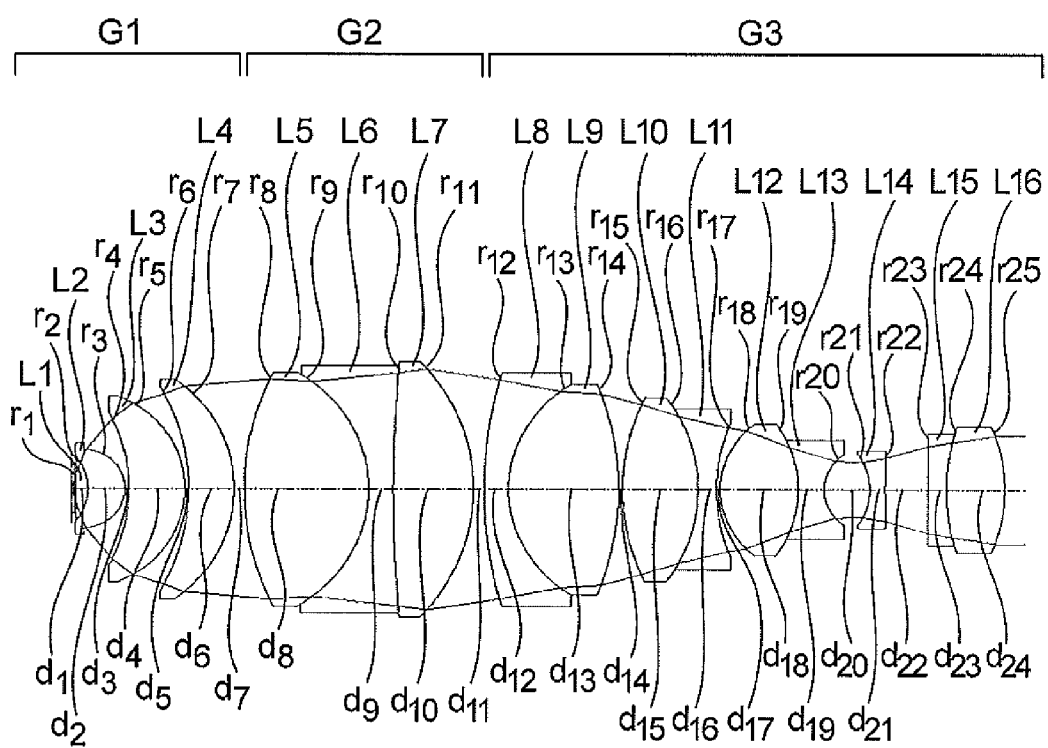
FIG. 2 is a cross-sectional view along an optical axis showing an optical arrangement of an immersion microscope objective according to a second example of the present invention.

Next, an objective according to the second example will be described below. The objective according to the second example, as shown in FIG. 2, includes in order from an object side, a first lens group G1, a second lens group G2, and a third lens group G3.

The first lens group G1 includes in order from the object side, a planoconvex positive lens L1, a positive meniscus lens L2 having a convex surface directed toward an image side, a positive meniscus lens L3 having a convex surface directed toward the image side, and a positive meniscus lens L4 having a convex surface directed toward the image side. Here, the planoconvex positive lens L1 and the positive meniscus lens L2 are cemented. This cemented lens is the first cemented lens.

The second lens group G2 includes in order from the object side, a biconvex positive lens L5, a biconcave negative lens 6, and a biconvex positive lens L7. Here, the biconvex positive lens L5, the biconcave negative lens L6, and the biconvex positive lens L7 are cemented. This cemented lens is the second cemented lens.

The third lens group G3 includes in order from the object side, a negative meniscus lens L8 having a convex surface directed toward the object side, a biconvex positive lens L9, a biconvex positive lens L10, a biconcave negative lens L11, a biconvex positive lens L12, a biconcave negative lens L13, a biconcave negative lens L14, a planoconcave negative lens L15, and a biconvex positive lens L16.

Here, the negative meniscus lens L8 and the biconvex positive lens L9 are cemented. Moreover, the biconvex positive lens L10 and the biconcave negative lens L11 are cemented. Moreover, the biconvex positive lens L12 and the biconcave negative lens L13 are cemented. Moreover, the planoconcave negative lens L15 and the biconvex positive lens L16 are cemented. A cemented lens of the planoconcave negative lens L15 and the biconvex positive lens L16 is the third cemented lens.

Moreover, the second lens group G2 moves relatively with respect to the first lens group G1 and the third lens group G3. At this time, a position of the first lens group G1 and a position of the third lens group G3 are fixed.

Figure 3:
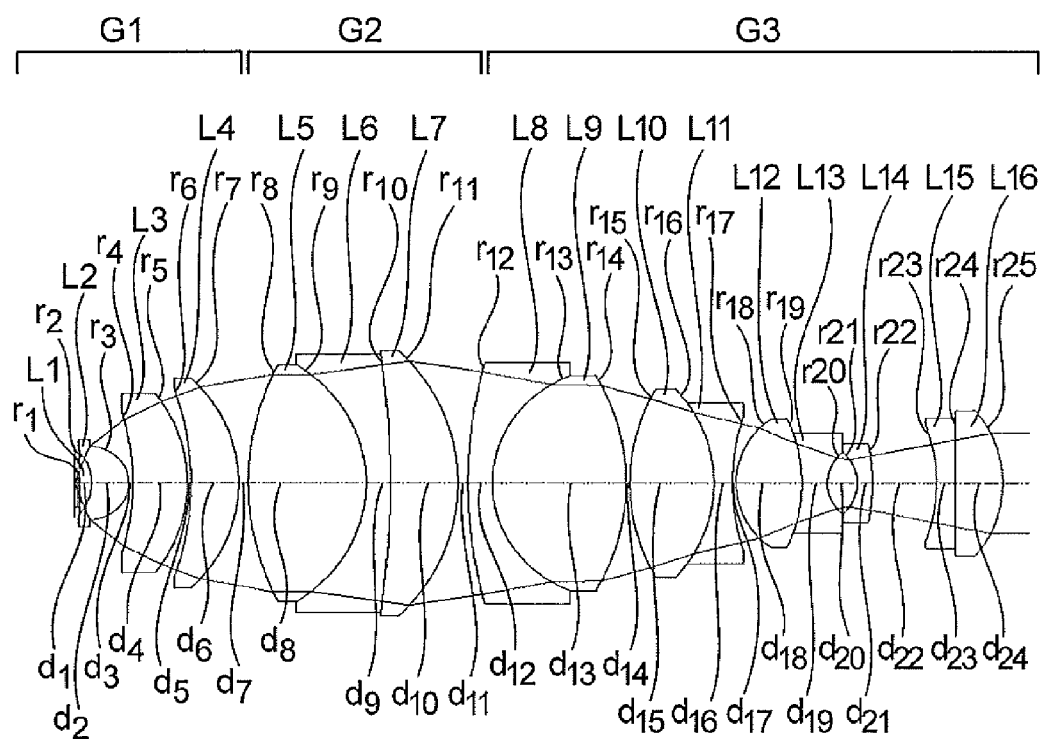
FIG. 3 is a cross-sectional view along an optical axis showing an optical arrangement of an immersion microscope objective according to a third example of the present invention.

Next, an objective according to the third example will be described below. The objective according to the third example, as shown in FIG. 3, includes in order from an object side, a first lens group G1, a second lens group G2, and a third lens group G3.

The first lens group G1 includes in order from the object side, a planoconvex positive lens L1, a positive meniscus lens L2 having a convex surface directed toward an image side, a positive meniscus lens L3 having a convex surface directed toward the image side, and a positive meniscus lens L4 having a convex surface directed toward the image side. Here, the planoconvex positive lens L1 and the positive meniscus lens L2 are cemented. This cemented lens is the first cemented lens.

The second lens group G2 includes in order from the object side, a biconvex positive lens L5, negative meniscus lens L6 having a convex surface directed toward the image side, and a positive meniscus lens L7 having a convex surface directed toward the object side. Here, the biconvex positive lens L5, the negative meniscus lens L6, and the positive meniscus lens L7 are cemented. This cemented lens is the second cemented lens.

The third lens group G3 includes in order from the object side, a negative meniscus lens L8 having a convex surface directed toward the object side, a biconvex positive lens L9, a biconvex positive lens L10, a biconcave negative lens L11, a biconvex positive lens L12, a biconcave negative lens L13, a negative meniscus lens L14 having a convex surface directed toward the image side, a negative meniscus lens L15 having a convex surface directed toward the image side, and a positive meniscus lens L16 having a convex surface directed toward the image side.

Here, the negative meniscus lens L8 and the biconvex positive lens L9 are cemented. Moreover, the biconvex positive lens L10 and the biconcave negative lens L11 are cemented. Moreover, the biconvex positive lens L12 and the biconcave negative lens L13 are cemented. Moreover, the negative meniscus lens L15 and the positive meniscus lens L16 are cemented. A cemented lens of the negative meniscus lens L15 and the positive meniscus lens L16 is the third cemented lens.

Moreover, the second lens group G2 moves relatively with respect to the first lens group G1 and the third lens group G3. At this time, a position of the first lens group G1 and a position of the third lens group G3 are fixed.

Figure 4:
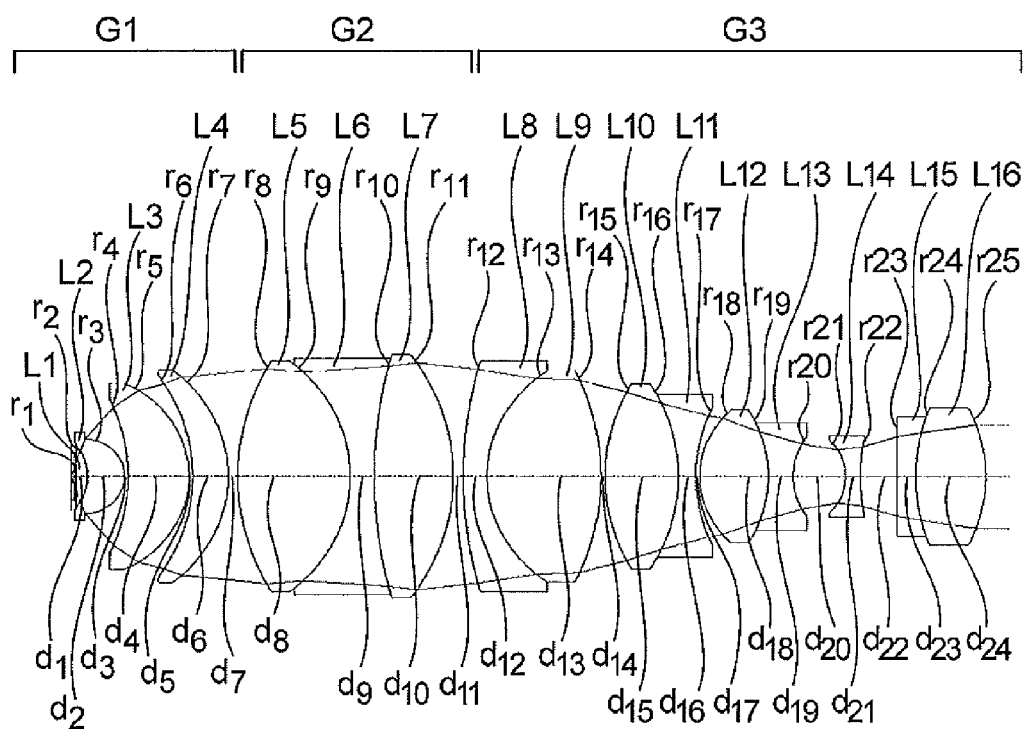
FIG. 4 is a cross-sectional view along an optical axis showing an optical arrangement of an immersion microscope objective according to a fourth example of the present invention.

Next, an objective according to the fourth example will be described below. The objective according to the fourth example, as shown in FIG. 4, includes in order from an object side, a first lens group G1, a second lens group G2, and a third lens group G3.

The first lens group G1 includes in order from the object side, a planoconvex positive lens L1, a positive meniscus lens L2 having a convex surface directed toward an image side, a positive meniscus lens L3 having a convex surface directed toward the image side, and a positive meniscus lens L4 having a convex surface directed toward the image side. Here, the planoconvex positive lens L1 and the positive meniscus lens L2 are cemented. This cemented lens is the first cemented lens.

The second lens group G2 includes in order from the object side, a biconvex positive lens L5, a biconcave negative lens L6, and a biconvex positive lens L7. Here, the biconvex positive lens L5, the biconcave negative lens L6, and the biconvex positive lens L7 are cemented. This cemented lens is the second cemented lens.

The third lens group G3 includes in order from the object side, a negative meniscus lens L8 having a convex surface directed toward the object side, a biconvex positive lens L9, a biconvex positive lens L10, a biconcave negative lens L11, a biconvex positive lens L12, a biconcave negative lens L13, a biconcave negative lens L14, a planoconcave negative lens L15, and a biconvex positive lens L16.

Here, the negative meniscus lens L8 and the biconvex positive lens L9 are cemented. Moreover, the biconvex positive lens L10 and the biconcave negative lens L11 are cemented. Moreover, the biconvex positive lens L12 and the biconcave negative lens L13 are cemented. Moreover the planoconcave negative lens L15 and the biconvex positive lens L16 are cemented. A cemented lens of the planoconcave negative lens L15 and the biconvex positive lens L16 is the third cemented lens.

Moreover, the second lens group G2 moves relatively with respect to the first lens group G1 and the third lens group G3. At this time, a position of the first lens group G1 and a position of the third lens group G3 are fixed.

Next, numerical data of optical members which form the immersion microscope objective according to each of the examples described above is given below. In the numerical data of each example, each of r1, r2, . . . denotes a radius of curvature of each lens surface, each of d1, d2, . . . denotes a thickness or an air space of each lens, each of nd1, nd2, . . . denotes a refractive index for a d-line of each lens, each of vd1, vd2, . . . denotes Abbe's number for each lens, NA denotes a numerical aperture, f denotes a focal length of the overall immersion microscope objective, and β denotes a magnification. The magnification β is a magnification when combined with a tube lens (focal length 180 mm) which will be described later.

Moreover, in various data, the temperature is a temperature in an environment in which the immersion microscope objective is used, WD is a distance from an object plate up to the lens L1 in the first lens group G1, and CG is a thickness of the cover glass.

Example 1

Unit mm
NA = 1.7, f = 1.8 mm, β = −100

Surface data

| Surface no. | r | d | nd | vd |
|---|---|---|---|---|
| 1 | ∞ | 0.6000 | 1.78800 | 47.37 |
| 2 | −2.8121 | 2.0000 | 1.88300 | 40.76 |
| 3 | −2.2317 | 0.2000 | | |
| 4 | −8.6188 | 3.0312 | 1.88300 | 40.76 |
| 5 | −5.6005 | 0.2000 | | |
| 6 | −10.3189 | 2.2512 | 1.59522 | 67.74 |
| 7 | −7.7701 | 0.5000 | | |
| 8 | 14.3914 | 6.5264 | 1.43875 | 94.93 |
| 9 | −7.9128 | 1.3000 | 1.67300 | 38.15 |
| 10 | 54.0360 | 4.1590 | 1.48875 | 94.93 |

-continued

Unit mm
NA = 1.7, f = 1.8 mm, β = −100

| | | | | |
|---|---:|---:|---:|---:|
| 11 | −10.6085 | 0.5500 | | |
| 12 | 23.2454 | 1.3000 | 1.63775 | 42.41 |
| 13 | 6.6996 | 5.9638 | 1.43875 | 94.93 |
| 14 | −18.8677 | 0.2000 | | |
| 15 | 9.3805 | 3.9213 | 1.49700 | 81.54 |
| 16 | −12.3493 | 0.9500 | 1.61340 | 44.27 |
| 17 | 7.6122 | 0.2000 | | |
| 18 | 4.5733 | 4.0853 | 1.49700 | 81.54 |
| 19 | −7.2942 | 1.3500 | 1.63775 | 42.41 |
| 20 | 2.3466 | 2.3673 | | |
| 21 | −3.2450 | 0.8000 | 1.61340 | 44.27 |
| 22 | −29.3240 | 2.2017 | | |
| 23 | ∞ | 1.0100 | 1.61340 | 44.27 |
| 24 | 12.1585 | 3.4688 | 1.73800 | 32.26 |
| 25 | −9.4691 | | | |

Various data
Temperature (degrees C.) 23

| | d | nd | νd |
|---|---:|---:|---:|
| CG | 0.15 | 1.78800 | 47.37 |
| WD | 0.125 | 1.78036 | 19.07 |

Example 2

Unit mm
NA = 1.7, f = 1.8 mm, β = −100

Surface data

| Surface no. | r | d | nd | νd |
|---|---:|---:|---:|---:|
| 1 | ∞ | 0.6000 | 1.78800 | 47.37 |
| 2 | −3.0000 | 2.0000 | 1.88300 | 40.76 |
| 3 | −2.2113 | 0.2000 | | |
| 4 | −9.2878 | 2.9694 | 1.88300 | 40.76 |
| 5 | −5.6822 | 0.2000 | | |
| 6 | −11.7360 | 2.3950 | 1.49700 | 81.54 |
| 7 | −7.7957 | Variable | | |
| 8 | 15.1688 | 6.5850 | 1.43875 | 94.93 |
| 9 | −7.7274 | 1.3000 | 1.67300 | 38.15 |
| 10 | 84.3318 | 4.2321 | 1.43875 | 94.93 |
| 11 | −10.6638 | Variable | | |
| 12 | 24.0333 | 1.3000 | 1.63775 | 42.41 |
| 13 | 7.0218 | 5.8915 | 1.43875 | 94.93 |
| 14 | −15.9911 | 0.2000 | | |
| 15 | 12.1854 | 4.0230 | 1.49700 | 81.54 |
| 16 | −8.8933 | 0.9500 | 1.61340 | 44.27 |
| 17 | 10.3207 | 0.2000 | | |
| 18 | 4.7830 | 4.1228 | 1.49700 | 81.54 |
| 19 | −6.4368 | 1.3500 | 1.63775 | 42.41 |
| 20 | 2.5014 | 2.4057 | | |
| 21 | −3.4454 | 0.8000 | 1.61340 | 44.27 |
| 22 | 154.6515 | 2.2255 | | |
| 23 | ∞ | 1.0100 | 1.61340 | 44.27 |
| 24 | 12.2963 | 3.1260 | 1.73800 | 32.26 |
| 25 | −8.9978 | | | |

Various data

| | Temperature (degrees C.) | |
|---|---:|---:|
| | 23 | 37 |
| CG | 0.15 | 0.15 |
| WD | 0.125 | 0.12539 |
| d7 | 0.5 | 0.59456 |
| d11 | 0.55 | 0.45544 |

| | d | nd | νd |
|---|---|---|---|

-continued

Unit mm
NA = 1.7, f = 1.8 mm, β = −100

Temperature 23 degrees C.

| CG | 0.15 | 1.78800 | 47.37 |
|---|---:|---:|---:|
| WD | 0.125 | 1.78036 | 19.07 |

Temperature 37 degrees C.

| CG | 0.15 | 1.78807 | 47.81 |
|---|---:|---:|---:|
| WD | 0.12539 | 1.77308 | 18.80 |

Example 3

Unit mm
NA = 1.6, f = 1.8 mm, β = −100

Surface data

| Surface no. | r | d | nd | νd |
|---|---:|---:|---:|---:|
| 1 | ∞ | 0.6000 | 1.67790 | 55.34 |
| 2 | −2.8292 | 2.0000 | 1.88300 | 40.76 |
| 3 | −2.0912 | 0.2000 | | |
| 4 | −14.5958 | 2.9155 | 1.88300 | 40.76 |
| 5 | −8.5871 | 0.2000 | | |
| 6 | −16.7090 | 2.4957 | 1.49700 | 81.54 |
| 7 | −8.5278 | Variable | | |
| 8 | 15.3226 | 6.2647 | 1.43875 | 94.93 |
| 9 | −8.0364 | 1.3000 | 1.67300 | 38.15 |
| 10 | −53.4747 | 3.6162 | 1.43875 | 94.93 |
| 11 | −10.6906 | Variable | | |
| 12 | 26.8416 | 1.3000 | 1.63775 | 42.41 |
| 13 | 6.6335 | 7.1593 | 1.43875 | 94.93 |
| 14 | −12.3861 | 0.2000 | | |
| 15 | 11.1783 | 4.4656 | 1.49700 | 81.54 |
| 16 | −8.1266 | 0.9500 | 1.61340 | 44.27 |
| 17 | 12.6626 | 0.2000 | | |
| 18 | 4.5664 | 3.5180 | 1.49700 | 81.54 |
| 19 | −8.8780 | 1.3500 | 1.63775 | 42.41 |
| 20 | 2.3388 | 1.5992 | | |
| 21 | −2.4056 | 0.8000 | 1.61340 | 44.27 |
| 22 | −12.5361 | 3.4215 | | |
| 23 | −9.5208 | 1.0100 | 1.61340 | 44.27 |
| 24 | −1266.5632 | 2.5201 | 1.73800 | 32.26 |
| 25 | −6.5738 | | | |

Various data

| | temperature (degrees C.) | |
|---|---:|---:|
| | 23 | 37 |
| CG | 0.15 | 0.15 |
| WD | 0.125 | 0.12729 |
| d7 | 0.5 | 0.50124 |
| d11 | 0.55 | 0.54876 |

| | d | nd | νd |
|---|---|---|---|

Temperature 23 degrees C.

| CG | 0.15 | 1.67790 | 55.34 |
|---|---:|---:|---:|
| WD | 0.125 | 1.67790 | 55.34 |

Temperature 37 degrees C.

| CG | 0.15 | 1.67791 | 55.29 |
|---|---:|---:|---:|
| WD | 0.12729 | 1.67791 | 55.29 |

Example 4

| | Unit mm | | |
|---|---|---|---|
| | NA = 1.7, f = 1.8 mm, β = −100 | | |

Surface data

| Surface no. | r | d | nd | vd |
|---|---|---|---|---|
| 1 | ∞ | 0.6000 | 1.78800 | 47.37 |
| 2 | −3.0000 | 2.0000 | 1.88300 | 40.76 |
| 3 | −2.1812 | 0.2000 | | |
| 4 | −10.6766 | 3.2618 | 1.88300 | 40.76 |
| 5 | −5.9699 | 0.2000 | | |
| 6 | −10.3020 | 1.9156 | 1.49700 | 81.54 |
| 7 | −7.8942 | Variable | | |
| 8 | 13.2426 | 6.0659 | 1.43875 | 94.93 |
| 9 | −8.5227 | 1.3000 | 1.67300 | 38.15 |
| 10 | 26.3880 | 4.2813 | 1.43875 | 94.93 |
| 11 | −12.0637 | Variable | | |
| 12 | 24.5564 | 1.3000 | 1.63775 | 42.41 |
| 13 | 7.4161 | 6.1606 | 1.43875 | 94.93 |
| 14 | −13.9866 | 0.2000 | | |
| 15 | 10.7829 | 3.9833 | 1.49700 | 81.54 |
| 16 | −10.1618 | 0.9500 | 1.61340 | 44.27 |
| 17 | 9.5751 | 0.2000 | | |
| 18 | 5.3076 | 3.6938 | 1.49700 | 81.54 |
| 19 | −7.5373 | 1.3500 | 1.63775 | 42.41 |
| 20 | 4.0260 | 2.8269 | | |
| 21 | −2.9913 | 0.8000 | 1.61340 | 44.27 |
| 22 | 12.1981 | 1.9575 | | |
| 23 | ∞ | 1.0100 | 1.61340 | 44.27 |
| 24 | 10.6675 | 3.8272 | 1.73800 | 32.26 |
| 25 | −8.6567 | | | |

Various data

| temperature (degrees C.) | | | |
|---|---|---|---|
| 23 | 23 | 23 | 37 |

| | | | | |
|---|---|---|---|---|
| CG | 0.13 | 0.15 | 0.17 | 0.15 |
| WD | 0.1449 | 0.1250 | 0.1053 | 0.1246 |
| d7 | 0.5064 | 0.5000 | 0.4792 | 0.6217 |
| d11 | 0.5436 | 0.5500 | 0.5708 | 0.4283 |

| | d | nd | vd |
|---|---|---|---|
| | Temperature 23 degrees C. | | |
| CG | 0.15 | 1.78800 | 47.37 |
| WD | 0.1250 | 1.78036 | 19.07 |
| | Temperature 37 degrees C. | | |
| CG | 0.15 | 1.78807 | 47.81 |
| WD | 0.1246 | 1.77308 | 18.80 |

Tube lens
Unit mm
Surface data

| Surface no. | r | d | nd | vd |
|---|---|---|---|---|
| 1 | 68.7541 | 7.7321 | 1.48749 | 70.21 |
| 2 | −37.5679 | 3.4742 | 1.80610 | 40.95 |
| 3 | −102.8477 | 0.6973 | | |
| 4 | 84.3099 | 6.0238 | 1.83400 | 37.17 |
| 5 | −50.7100 | 3.0298 | 1.64450 | 40.82 |
| 6 | 40.6619 | | | |
| f | 180 | | | |

FIGS. 5A to 5D through FIGS. 13A to 13D are aberration diagrams of immersion microscope objective according to the first to fourth examples in the following conditions.

Figure 5:
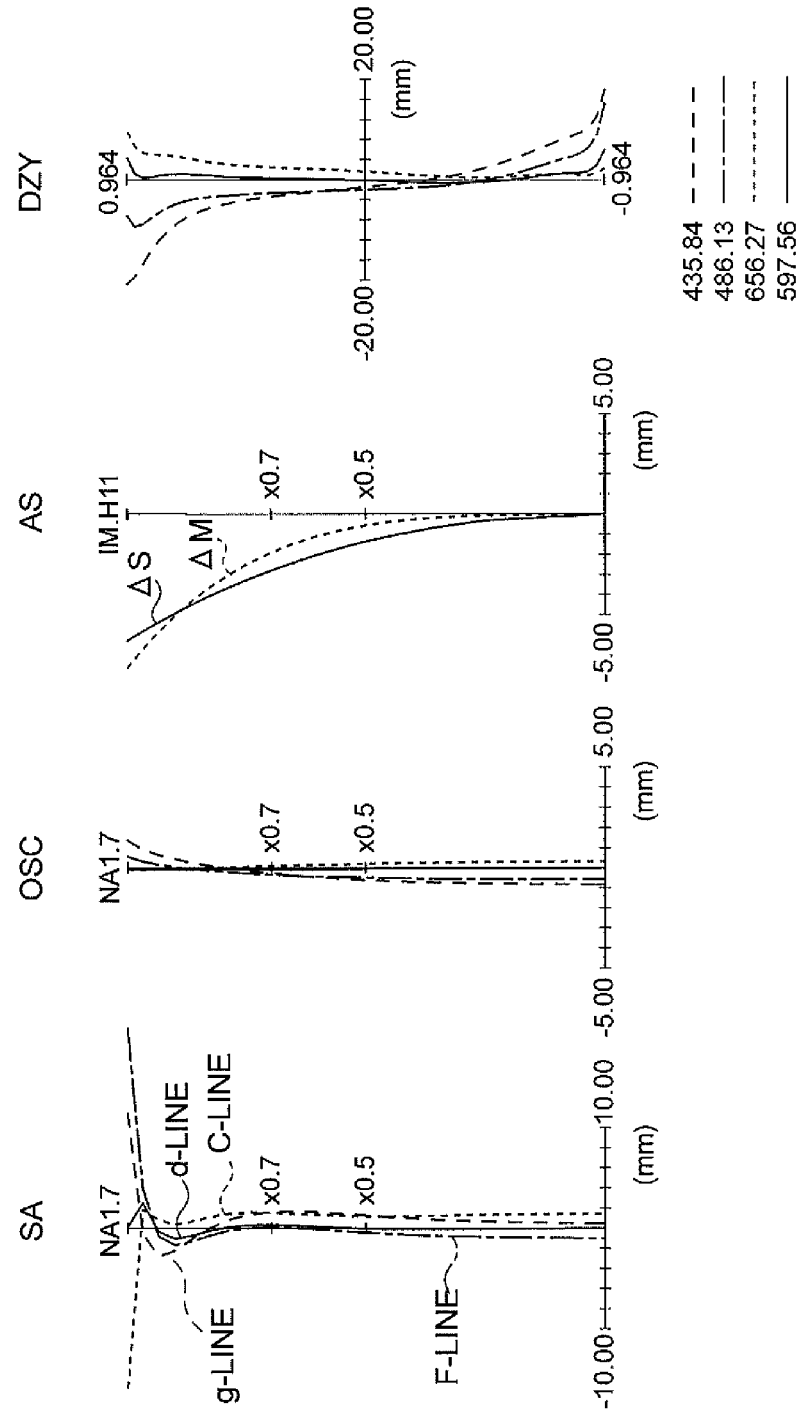
FIG. 5A, FIG. 5B, FIG. 5C, and FIG. 5D are aberration diagrams of the immersion microscope objective according to the first example, and are diagrams when an operating temperature is 23 degrees C.
Figure 6:
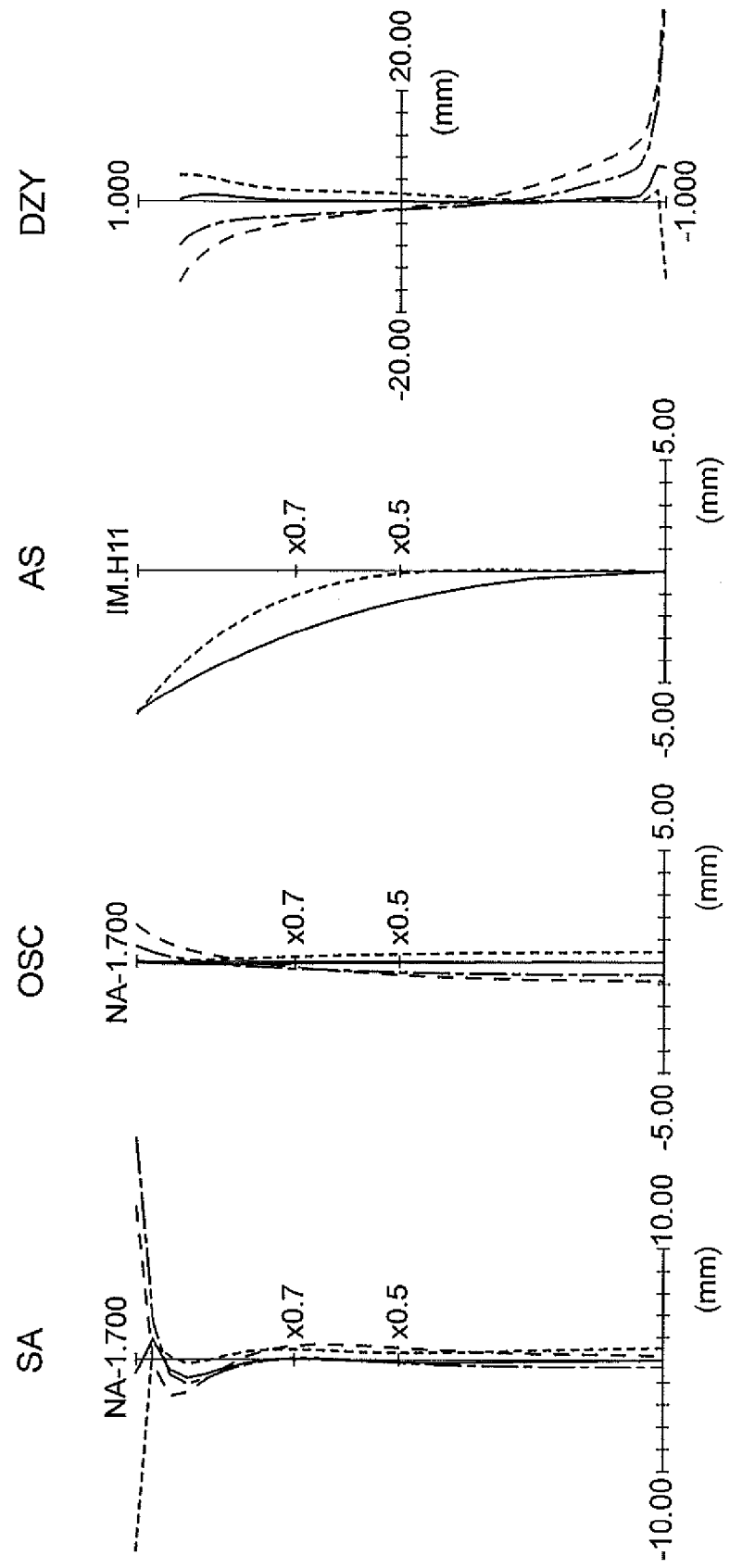
FIG. 6A, FIG. 6B, FIG. 6C, and FIG. 6D are aberration diagrams of the immersion microscope objective according to the second example, and are diagrams when an operating temperature is 23 degrees C.
Figure 7:
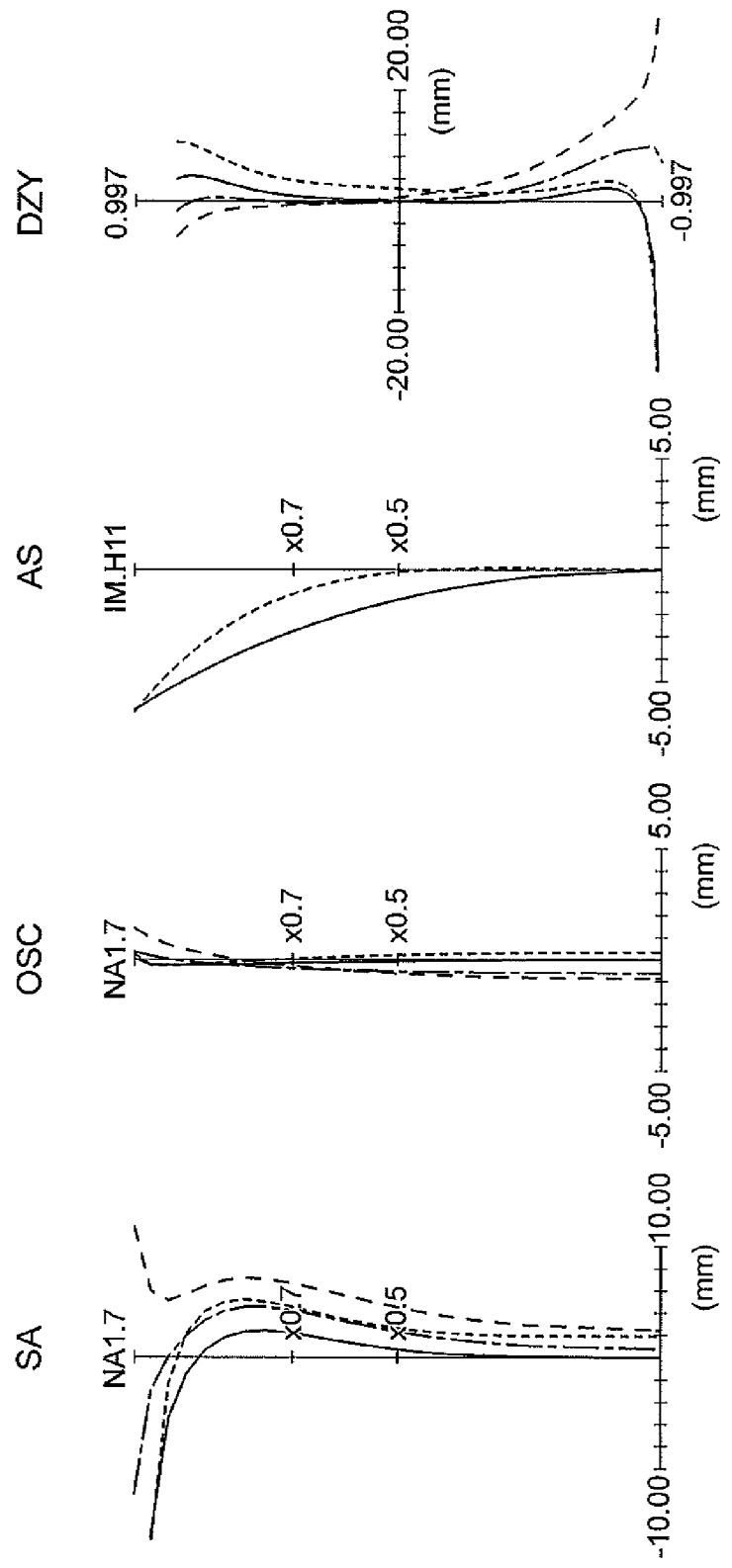
FIG. 7A, FIG. 7B, FIG. 7C, and FIG. 7D are aberration diagrams of the immersion microscope objective according to the second example, and are diagrams when the operating temperature is 37 degrees C.
Figure 8:
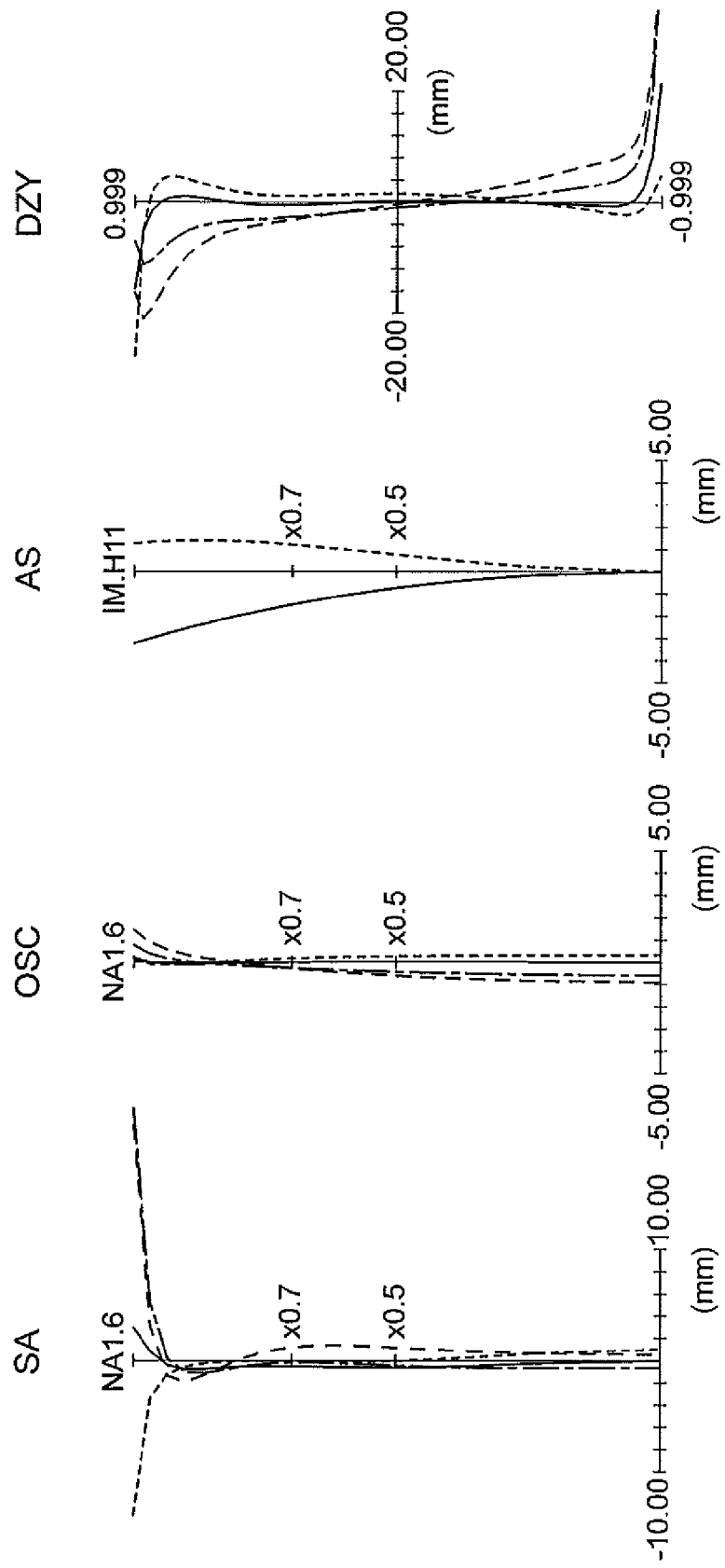
FIG. 8A, FIG. 8B, FIG. 8C, and FIG. 8D are aberration diagrams of the immersion microscope objective according to the third example, and are diagrams when an operating temperature is 23 degrees C.
Figure 9:
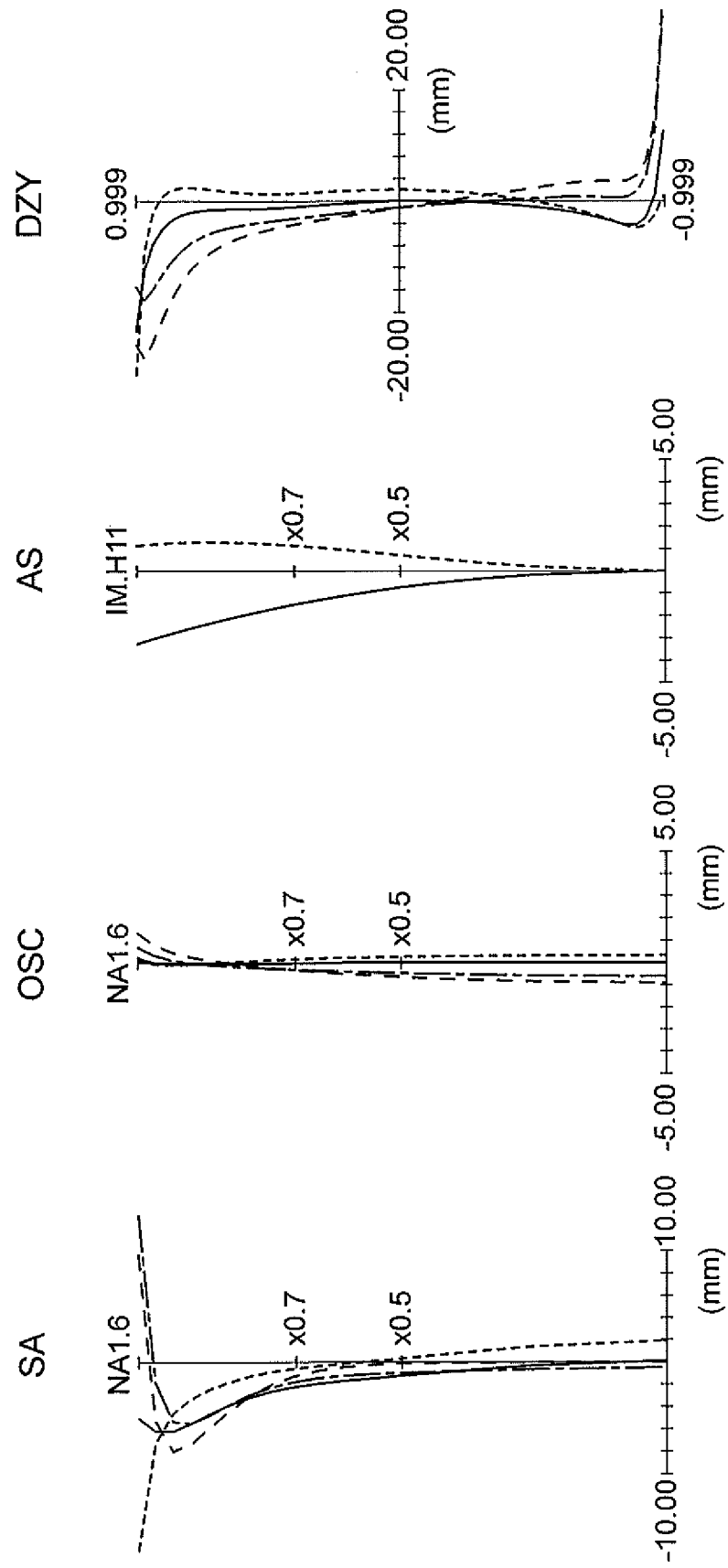
FIG. 9A, FIG. 9B, FIG. 9C, and FIG. 9D are aberration diagrams of the immersion microscope objective according to the third example, and are diagrams when the operating temperature is 37 degrees C.
Figure 10:
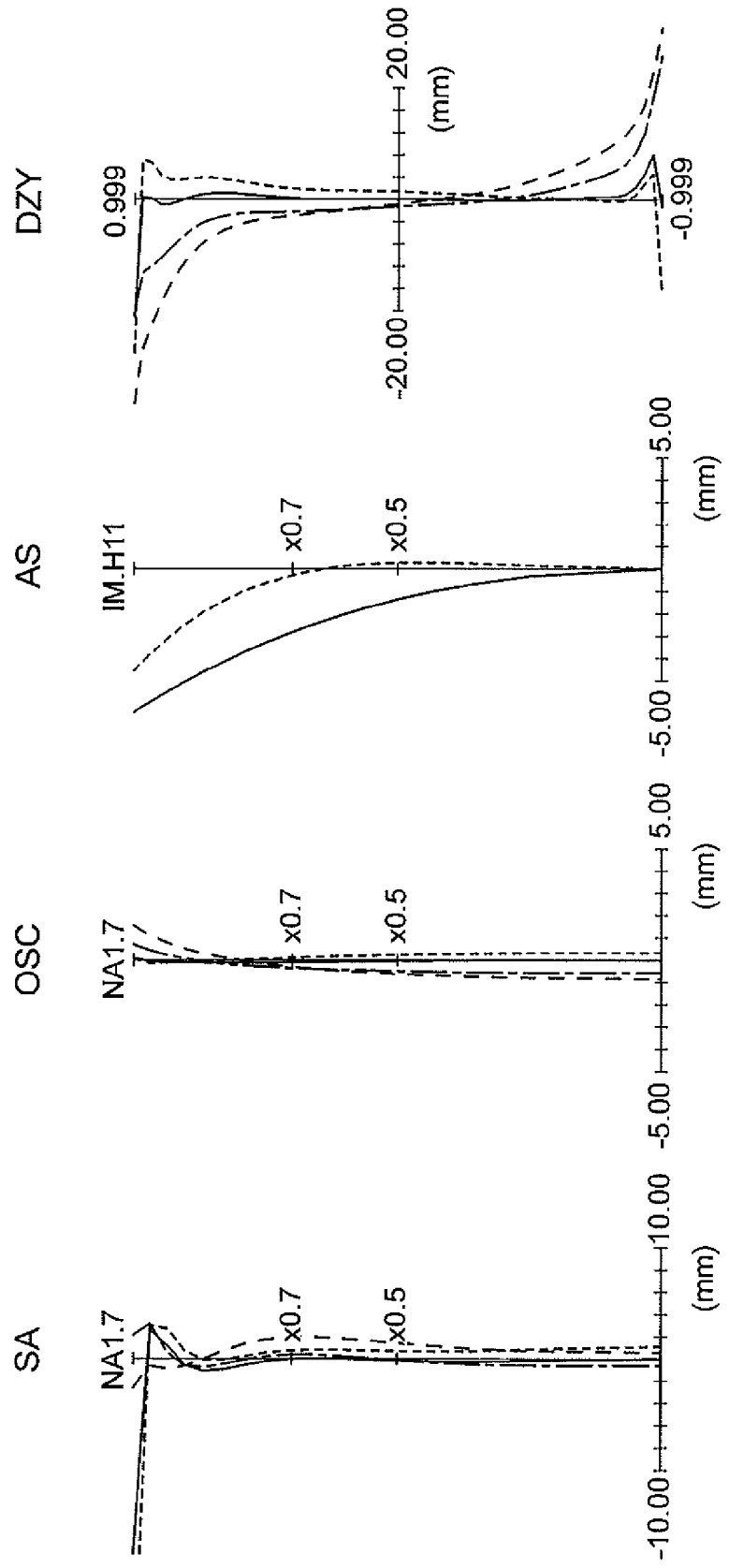
FIG. 10A, FIG. 10B, FIG. 10C, and FIG. 10D are aberration diagrams of the immersion microscope objective according to the fourth example, and are diagrams when an operating temperature is 23 degrees C. and a cover-glass thickness is 0.13 mm.
Figure 11:
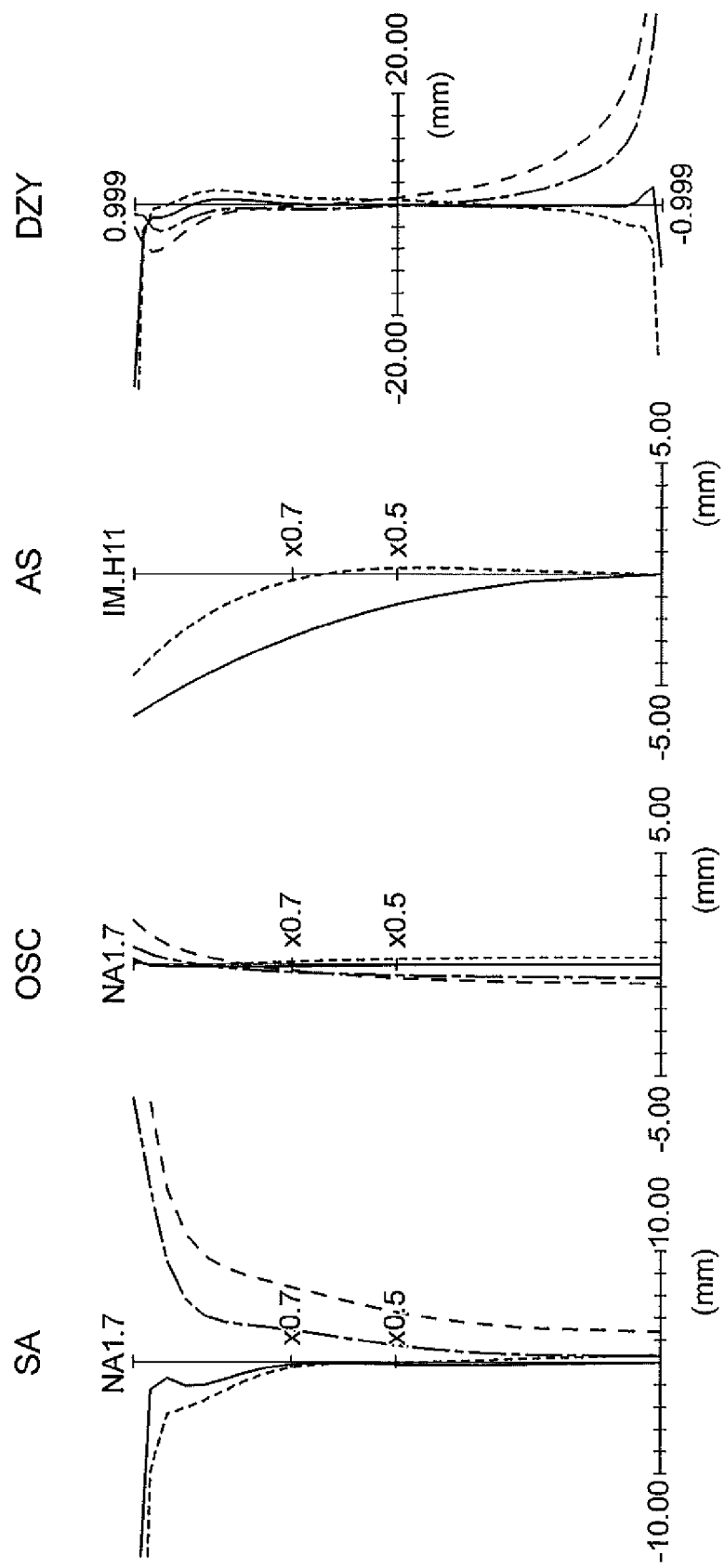
FIG. 11A, FIG. 11B, FIG. 11C, and FIG. 11D are aberration diagrams of the immersion microscope objective according to the fourth example, and are diagrams when the operating temperature is 23 degrees C. and the cover-glass thickness is 0.15 mm.
Figure 12:
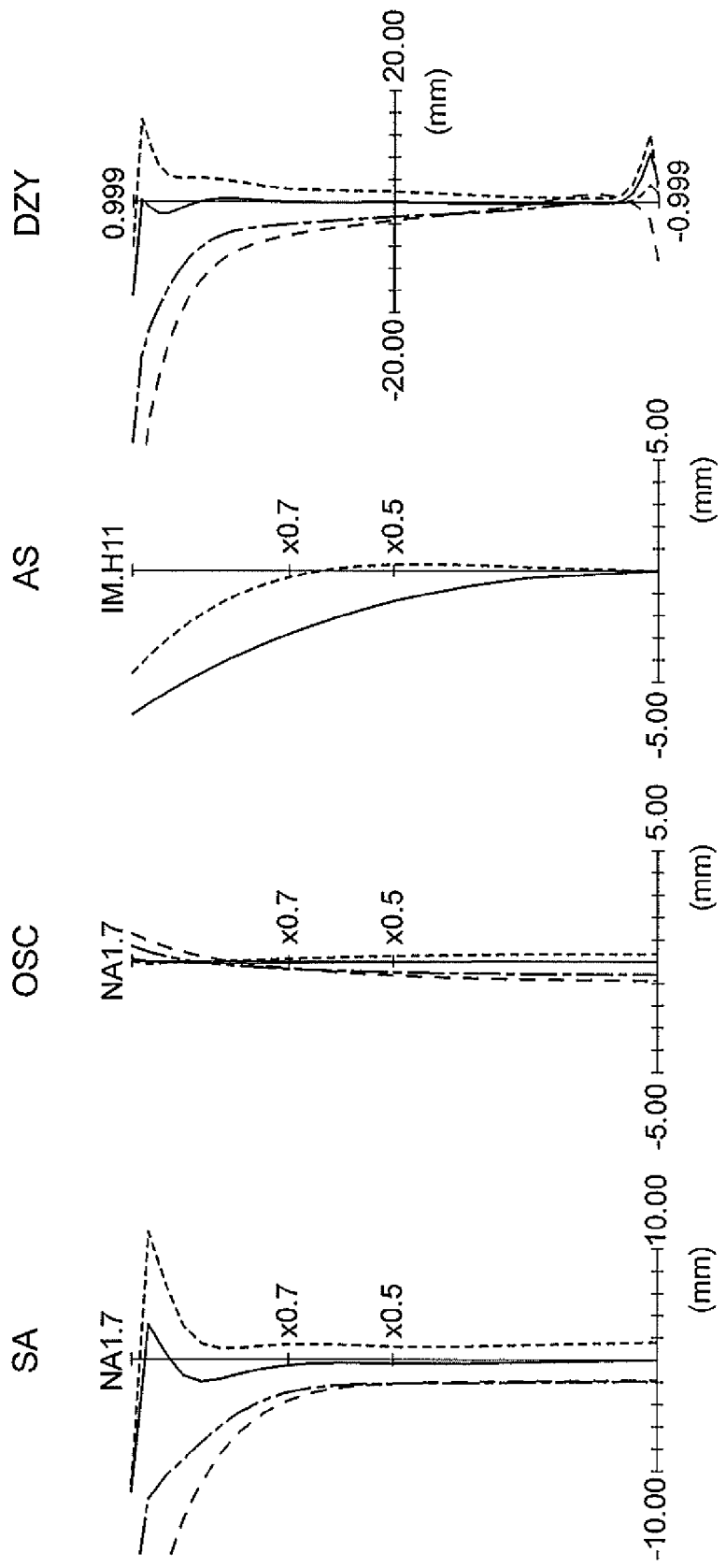
FIG. 12A, FIG. 12B, FIG. 12C, and FIG. 12D are aberration diagrams of the immersion microscope objective according to the fourth example, and are diagrams when the operating temperature is 23 degrees C., and the cover-glass thickness is 0.17 mm.
Figure 13:
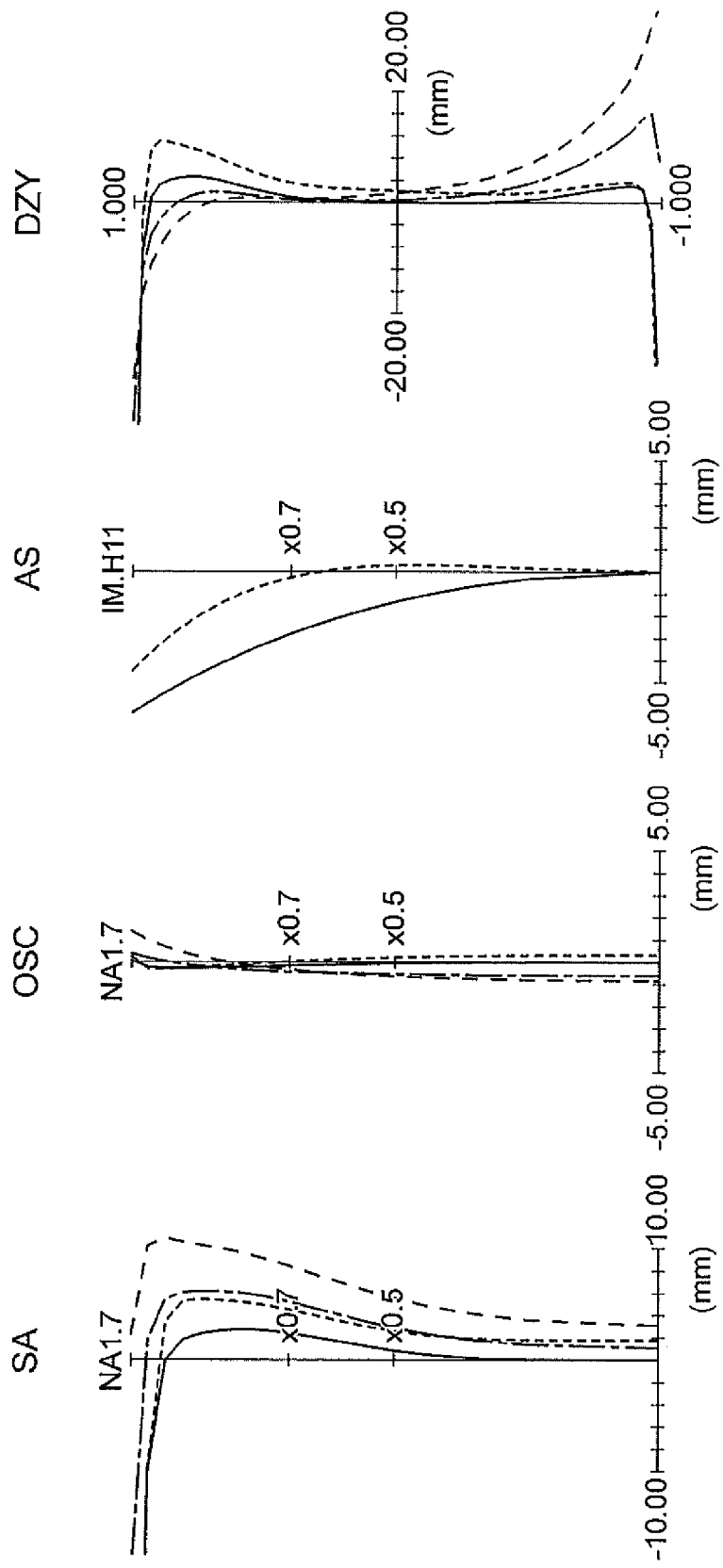
FIG. 13A, FIG. 13B, FIG. 13C, and FIG. 13D are aberration diagrams of the immersion microscope objective according to the fourth example, and are diagrams when the operating temperature is 37 degrees C., and the cover-glass thickness is 0.15 mm

| | Example | thickness of CG | operating temperature |
|---|---|---|---|
| FIG. 5 | Example 1 | 0.15 mm | 23 degrees C. |
| FIG. 6 | Example 2 | 0.15 mm | 23 degrees C. |
| FIG. 7 | Example 2 | 0.15 mm | 37 degrees C. |
| FIG. 8 | Example 3 | 0.15 mm | 23 degrees C. |
| FIG. 9 | Example 3 | 0.15 mm | 37 degrees C. |
| FIG. 10 | Example 4 | 0.13 mm | 23 degrees C. |
| FIG. 11 | Example 4 | 0.15 mm | 23 degrees C. |
| FIG. 12 | Example 4 | 0.17 mm | 23 degrees C. |
| FIG. 13 | Example 4 | 0.15 mm | 37 degrees C. |

Moreover, in the aberration diagrams, 'IM. H' denotes an image height. Diagram numbers, suffixed A, B, C, and D denote spherical aberration (SA), offense against the sine condition (OSC), astigmatism (AS), and somatic aberration (DZY) A vertical axis in the (somatic aberration (DZY) is an image-height ratio.

Next, the values of conditional expressions (1) to (6) in each example are shown below.

| Conditional expression | Ex. 1 | Ex. 2 | Ex. 3 | Ex. 4 |
|---|---|---|---|---|
| (1) $(n_0/n_{1o})/NA_{ob}$ | 0.5857 | 0.5857 | 0.6250 | 0.5857 |
| (2) $r_{1c}/r_{1i}$ | 1.260 | 1.357 | 1.353 | 1.375 |
| (3) $(d_{1o} \times n_{1o})/(d_{1i} \times n_{1i})$ | 0.285 | 0.285 | 0.267 | 0.285 |
| (4) $f_1/d_1$ | 0.365 | 0.350 | 0.339 | 0.352 |
| (5) $n_{1H} - n_{1L}$ | 0.288 | 0.386 | 0.386 | 0.386 |
| (6) $f_{32o}/f_{32}$ | 0.0296 | 0.053 | 0.198 | 0.167 |

Further, the values of the parameters in the respective conditions conditional expressions (1) to (6) are shown below.

| Parameter | Ex. 1 | Ex. 2 | Ex. 3 | Ex. 4 |
|---|---|---|---|---|
| $NA_{ob}$ | 1.700 | 1.700 | 1.600 | 1.700 |
| $n_0$ | 1.780 | 1.780 | 1.678 | 1.780 |
| $n_{1o}$ | 1.788 | 1.788 | 1.6779 | 1.788 |
| $r_{1c}$ | −2.8121 | −3.000 | −2.8292 | −3.000 |
| $r_{1i}$ | −2.2317 | −2.2113 | −2.0912 | −2.1812 |
| $d_{1o}$ | 0.600 | 0.600 | 0.600 | 0.600 |
| $d_{1i}$ | 2.000 | 2.000 | 2.000 | 2.000 |
| $n_{1i}$ | 1.883 | 1.883 | 1.883 | 1.883 |
| $f_1$ | 3.021 | 2.931 | 2.853 | 2.882 |
| $d_1$ | 8.2824 | 8.3644 | 8.4112 | 8.1774 |
| $n_{1H}$ | 1.883 | 1.883 | 1.883 | 1.883 |
| $n_{1L}$ | 1.59522 | 1.497 | 1.497 | 1.497 |
| $f_{32o}$ | −6.019 | −5.484 | −5.003 | −3.839 |
| $f_{32}$ | −203.44 | −103.64 | −25.208 | −23.020 |

Figure 15:
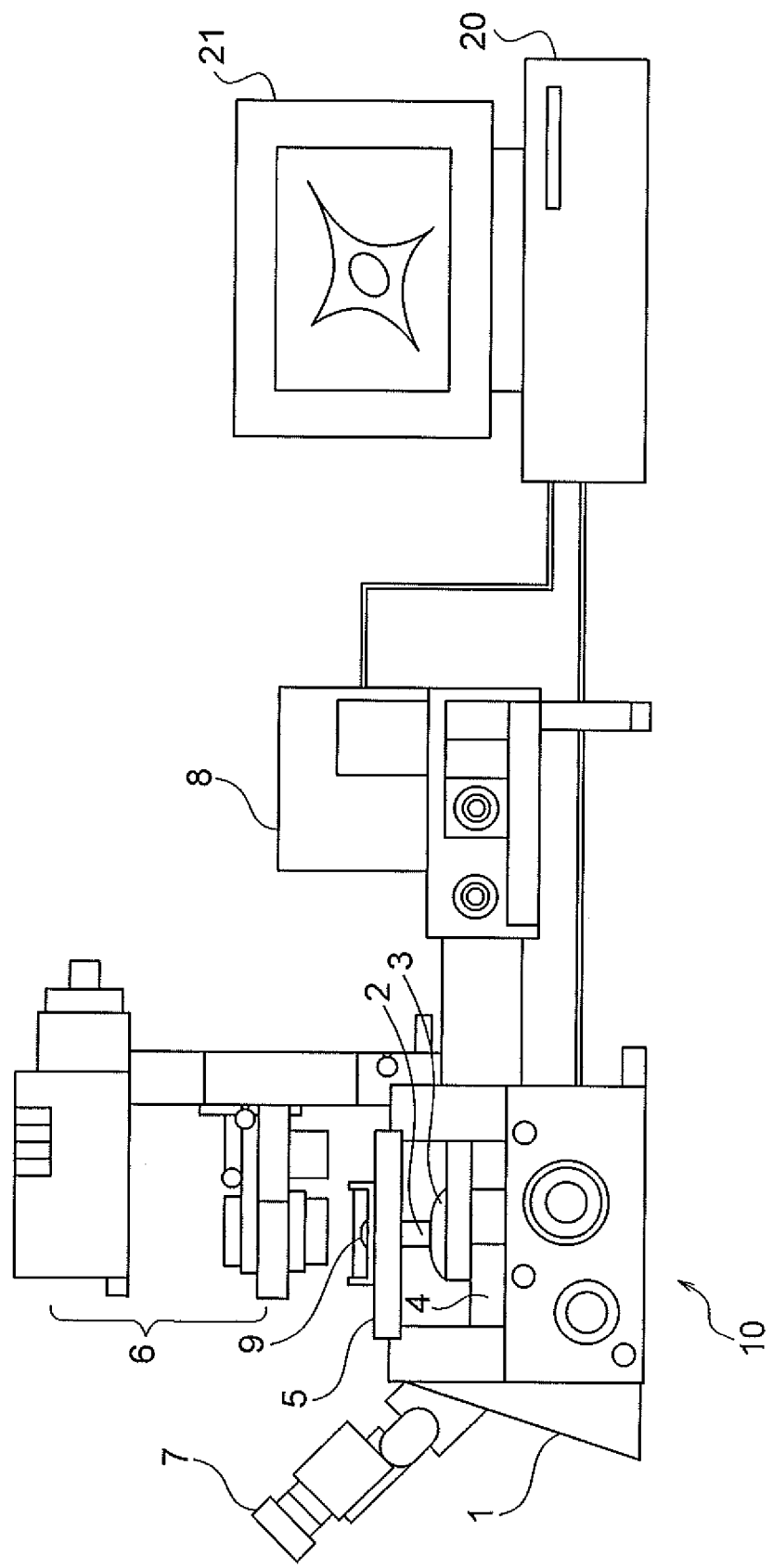
FIG. 15 is a diagram of a microscope in which, the immersion microscope objective according to the present invention is used.

FIG. 15 is a diagram showing the microscope according to the present embodiment. In FIG. 15, an example of an external structure of a laser scanning confocal microscope is shown as an example of the microscope. As shown in FIG. 15, a microscope 10 includes a main body 1, an objective 2, a revolver 3, an objective raising and lowering mechanism 4, a stage 5, an epi-illumination unit 6, an observation lens barrel 7, and a confocal scanner 8. Moreover, an image processing apparatus 20 is connected to the microscope 10, and an image display apparatus 21 is connected to the image processing apparatus 20. In the microscope according to the present embodiment, the immersion microscope objective according to the present embodiment is used for the objective 2.

The stage 5 is provided to the main body 1. A sample 9 is to be placed on the stage 5. Moreover, the episcopic illumination unit 6 is provided at an upper side of the main body 1. Illumination light is irradiated to the sample 9 by the episcopic illumination unit 6. Light from the sample 9 travels through the objective 2, and reaches the observation lens barrel 7. A user is able to observe the sample 9 through the observation lens barrel 7.

Moreover, a laser source (not shown in the diagram) and the confocal scanner 8 are provided at a rear side (right side of a paper surface) of the main body 1. The laser source and the confocal scanner 8 are connected by a fiber (not shown in the diagram). The confocal scanner 8 includes a galvanometer scanner, a pin hole, and a photo detection element, which are disposed at an interior of the confocal scanner 8. Light from the laser source, after travelling through the confocal scanner 8 is incident on the objective 2. The objective 2 is positioned at a lower side of the stage 5. Therefore, the sample 9 is illuminated from a lower side as well.

Light (reflected light or fluorescent light) from the sample 9, upon travelling through the objective 2, passes through the pin hole of the confocal scanner 8, and is detected by the photo detection element. Accordingly, a confocal observation is possible. In the confocal observation, it is possible to obtain a cross-sectional image of the sample 9.

The objective raising and lowering mechanism 4 is connected to the revolver 3. The objective raising and lowering mechanism 4 is capable of moving the objective 2 (the revolver 3) along an optical axial direction. In a case in which, a plurality of cross-sectional images along the optical axial direction of the sample 9 are to be obtained, the objective 2 is to be moved by the objective raising and lowering mechanism 4.

A signal obtained by the confocal scanner 8 is transmitted to the image processing apparatus 20. An image processing is carried out in the image processing apparatus 20, and an image of the sample 9 is displayed on the image display apparatus 21.

In the example described above, the immersion microscope objective according to the present embodiment has been used for confocal observation. However, it is also possible to use the immersion microscope objective according to the present embodiment for a total internal reflection fluorescence observation. In such case, a diameter of a bundle of rays from the laser source is to be kept smaller than an effective aperture of the immersion microscope objective. Moreover, an arrangement is to be made such that, the bundle of rays from the laser source is made to be incident on the immersion microscope objective such that it does not include an optical axis of the immersion microscope objective. Moreover, fluorescence from the sample is to be detected by the photo detection element without allowing passing through the pin hole.

The present invention can have various modified examples without departing from the scope of the invention.

As it has been described above, the present invention is suitable for an immersion microscope objective having a large numerical aperture, in which, the spherical aberration and the chromatic aberration are corrected sufficiently, or for an immersion microscope objective having a large numerical aperture which is capable of maintaining favorable image forming performance even when there is a variation in the thickness of the cover glass or when there is a change in temperature of the environment in which the immersion microscope objective is used, and a microscope using the immersion microscope objective.

What is claimed is:

1. A microscope objective comprising in order from an object side:
   a first lens group;
   a second lens group; and
   a third lens group, wherein:
   the first lens group includes a first cemented lens, and at least one positive single lens,
   the second lens group includes a second cemented lens, and changes a divergent bundle of rays to a convergent bundle of rays,
   the third lens group includes in order from the object side, a first lens component and a second lens component,
   a positive lens and a meniscus lens are cemented in the first cemented lens,
   a surface nearest to an image side of the first lens component is a concave surface directed toward the image side,
   a surface nearest to the object side of the second lens component is a concave surface directed toward the object side,
   the first lens component and the second lens component are disposed such that the concave surface of the first lens component and the concave surface of the second lens component are face-to-face, and
   the following conditional expression (1) is satisfied;

$$0.5 < (n_0/n_{1o})/NA_{ob} < 0.65 \qquad (1)$$

where,
$NA_{ob}$ denotes an object-side numerical aperture of the microscope objective,
$n_0$ denotes a refractive index for a d-line of a medium on the object side of the positive lens, and
$n_{1o}$ denotes a refractive index for a d-line of the positive lens.

2. The microscope objective according to claim 1, wherein the first lens group includes a plurality of positive single lenses, and
the following conditional expression (2) is satisfied;

$$1 < r_{1c}/r_{1i} < 2 \qquad (2)$$

where,
$r_{1c}$ denotes a radius of curvature of a cemented surface of the first cemented lens, and
$r_{1i}$ denotes a radius of curvature of an image-side surface of the first cemented lens.

3. The microscope objective according to claim 2, wherein the following conditional expression (5) is satisfied;

$$0.2 < n_{1H} - n_{1L} < 0.6 \qquad (5)$$

where,
$n_{1H}$ denotes a highest refractive index for a d-line of one of the plurality of positive single lenses, and
$n_{1L}$ denotes a lowest refractive index for a d-line of another one of the plurality of positive single lenses.

4. The microscope objective according to claim 1, wherein the following conditional expression (3) is satisfied;

$$0.2 < (d_{1o} \times n_{1o})/(d_{1i} \times n_{1i}) < 1 \qquad (3)$$

where,
$d_{1o}$ denotes an optical axial thickness of the positive lens,
$n_{1o}$ denotes the refractive index for the d-line of the positive lens,
$d_{1i}$ denotes an optical axial thickness of the meniscus lens, and
$n_{1i}$ denotes a refractive index for a d-line of the meniscus lens.

5. The microscope objective according to claim 1, wherein the following conditional expression (4) is satisfied;

$$0.2 < f_1/d_1 < 0.45 \qquad (4)$$

where,
$f_1$ denotes a focal length of the first lens group, and
$d_1$ denotes an overall length of the first lens group.

6. The microscope objective according to claim 1, wherein the second lens component includes an object-side lens and a third cemented lens, and a height of an axial marginal ray is the maximum at the third cemented lens of the second lens component, and is the minimum at a surface nearest to the object side of the second lens component, and the following conditional expression (6) is satisfied;

$$0 \leq f_{32o}/f_{32} < 0.45 \quad (6)$$

where, $f_{32o}$ denotes a focal length of the object-side lens, and
$f_{32}$ denotes a focal length of the second lens component.

7. The microscope objective according to claim 1, wherein one of the first lens group, the second lens group, and the third lens group moves along an optical axis.

8. A microscope comprising:
a light source;
an illumination optical system;
a main-body section;
an observation optical system; and
the microscope objective according to claim 1.

9. The microscope objective according to claim 1, wherein the following conditional expression (3') is satisfied;

$$0.25 < (d_{1o} \times n_{1o})/(d_{1i} \times n_{1i}) < 0.4 \quad (3')$$

where, $d_{1o}$ denotes an optical axial thickness of the positive lens,
$n_{1o}$ denotes the refractive index for the d-line of the positive lens,
$d_{1i}$ denotes an optical axial thickness of the meniscus lens, and
$n_{1i}$ denotes a refractive index for a d-line of the meniscus lens.

* * * * *